United States Patent
Dreyfuss et al.

(10) Patent No.: US 8,227,203 B2
(45) Date of Patent: Jul. 24, 2012

(54) METHOD FOR TESTING OR SCREENING PROTEIN SYNTHESIS INHIBITORS

(75) Inventors: Gideon Dreyfuss, Wynnewood, PA (US); Mumtaz Kasim, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 213 days.

(21) Appl. No.: 12/663,161

(22) PCT Filed: Jun. 4, 2008

(86) PCT No.: PCT/US2008/006972
§ 371 (c)(1),
(2), (4) Date: Jun. 30, 2010

(87) PCT Pub. No.: WO2008/150515
PCT Pub. Date: Dec. 11, 2008

(65) Prior Publication Data
US 2010/0273179 A1    Oct. 28, 2010

Related U.S. Application Data

(60) Provisional application No. 60/924,883, filed on Jun. 4, 2007.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 422/50; 530/300; 530/350

(58) Field of Classification Search .................. None
See application file for complete search history.

(56) References Cited

U.S. PATENT DOCUMENTS
2006/0223092 A1   10/2006  Dreyfuss

OTHER PUBLICATIONS

Fierro-Monti et al. Quantitative Proteomics Identifies Gemin5, A Scaffolding Protein Involved in Ribonucleoprotein Assembly, as a Novel Partner for Eukaryotic Initiation Factor 4E *J. Proteome Res.*, 2006, 5 (6), pp. 1367-1378.
Shpargel et al. Gemin proteins are required for efficient assembly of Sm-class ribonucleoproteins. Proc Natl Acad Sci (USA) Nov. 2005, 102(48): 17372-17377,-abstract.
Liu et al. The Spinal Muscular Atrophy Disease Gene Product, SMN, and its Associated Protein SIP1 Are in a Complex with Spliceosomal snRNP Proteins, Cell Sep 1997, 90(18): 1013-1021; p. 1015 right col. para 3: p. 1016 Fig 3, og 1015 Fig 2B legend.
Meister et al. SMN-mediated assembly of RNP's; a complex story, Trends in Cell Biology 2002, 12(10); 472-278.

*Primary Examiner* — Lisa Cook
(74) *Attorney, Agent, or Firm* — Mark S. Cohen; Pearl Cohen Zedek Latzer, LLP

(57) ABSTRACT

This invention provides methods for screening an inhibitor of protein synthesis by measuring the level of relocalization of an SMN complex component from the cytoplasm to the nucleus. Additionally, the invention provides a kit and a system for screening protein synthesis inhibitors in a cell.

18 Claims, 4 Drawing Sheets

SEQUENCE LISTING

```
<160> NUMBER OF SEQ ID NOS: 14

<210> SEQ ID NO 1
<211> LENGTH: 294
<212> TYPE: PRT
<213> ORGANISM: Homo sapiens

<400> SEQUENCE: 1

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240
```

```
Pro Ile Ile Pro Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
        260                 265                 270

His Thr Gly Tyr Tyr Met Gly Phe Arg Gln Asn Gln Lys Glu Gly Arg
            275                 280                 285

Cys Ser His Ser Leu Asn
        290

<210> SEQ ID NO 2
<211> LENGTH: 280
<212> TYPE: PRT
<213> ORGANISM: Homo sapiens

<400> SEQUENCE: 2

Met Arg Arg Ala Glu Leu Ala Gly Leu Lys Thr Met Ala Trp Val Pro
1               5                   10                  15

Ala Glu Ser Ala Val Glu Glu Leu Met Pro Arg Leu Leu Pro Val Glu
            20                  25                  30

Pro Cys Asp Leu Thr Glu Gly Phe Asp Pro Ser Val Pro Pro Arg Thr
        35                  40                  45

Pro Gln Glu Tyr Leu Arg Arg Val Gln Ile Glu Ala Ala Gln Cys Pro
    50                  55                  60

Asp Val Val Val Ala Gln Ile Asp Pro Lys Lys Leu Lys Arg Lys Gln
65                  70                  75                  80

Ser Val Asn Ile Ser Leu Ser Gly Cys Gln Pro Ala Pro Glu Gly Tyr
                85                  90                  95

Ser Pro Thr Leu Gln Trp Gln Gln Gln Val Ala Gln Phe Ser Thr
            100                 105                 110

Val Arg Gln Asn Val Asn Lys His Arg Ser His Trp Lys Ser Gln Gln
        115                 120                 125

Leu Asp Ser Asn Val Thr Met Pro Lys Ser Glu Asp Glu Glu Gly Trp
    130                 135                 140

Lys Lys Phe Cys Leu Gly Glu Lys Leu Cys Ala Asp Gly Ala Val Gly
145                 150                 155                 160

Pro Ala Thr Asn Glu Ser Pro Gly Ile Asp Tyr Val Gln Ile Gly Phe
                165                 170                 175

Pro Pro Leu Leu Ser Ile Val Ser Arg Met Asn Gln Ala Thr Val Thr
            180                 185                 190

Ser Val Leu Glu Tyr Leu Ser Asn Trp Phe Gly Glu Arg Asp Phe Thr
        195                 200                 205

Pro Glu Leu Gly Arg Trp Leu Tyr Ala Leu Leu Ala Cys Leu Glu Lys
    210                 215                 220

Pro Leu Leu Pro Glu Ala His Ser Leu Ile Arg Gln Leu Ala Arg Arg
225                 230                 235                 240

Cys Ser Glu Val Arg Leu Leu Val Asp Ser Lys Asp Asp Glu Arg Val
                245                 250                 255

Pro Ala Leu Asn Leu Leu Ile Cys Leu Val Ser Arg Tyr Phe Asp Gln
            260                 265                 270

Arg Asp Leu Ala Asp Glu Pro Ser
        275                 280

<210> SEQ ID NO 3
<211> LENGTH: 824
<212> TYPE: PRT
<213> ORGANISM: Homo sapiens
```

<400> SEQUENCE: 3

```
Met Ala Ala Ala Phe Glu Ala Ser Gly Ala Leu Ala Val Ala Thr
1               5                   10                  15

Ala Met Pro Ala Glu His Val Ala Val Gln Val Pro Ala Pro Glu Pro
            20                  25                  30

Thr Pro Gly Pro Val Arg Ile Leu Arg Thr Ala Gln Asp Leu Ser Ser
                35                  40                  45

Pro Arg Thr Arg Thr Gly Asp Val Leu Leu Ala Glu Pro Ala Asp Phe
    50                  55                  60

Glu Ser Leu Leu Leu Ser Arg Pro Val Leu Glu Gly Leu Arg Ala Ala
65                  70                  75                  80

Gly Phe Glu Arg Pro Ser Pro Val Gln Leu Lys Ala Ile Pro Leu Gly
                85                  90                  95

Arg Cys Gly Leu Asp Leu Ile Val Gln Ala Lys Ser Gly Thr Gly Lys
                100                 105                 110

Thr Cys Val Phe Ser Thr Ile Ala Leu Asp Ser Leu Val Leu Glu Asn
                115                 120                 125

Leu Ser Thr Gln Ile Leu Ile Leu Ala Pro Thr Arg Glu Ile Ala Val
130                 135                 140

Gln Ile His Ser Val Ile Thr Ala Ile Gly Ile Lys Met Glu Gly Leu
145                 150                 155                 160

Glu Cys His Val Phe Ile Gly Gly Thr Pro Leu Ser Gln Asp Lys Thr
                165                 170                 175

Arg Leu Lys Lys Cys His Ile Ala Val Gly Ser Pro Gly Arg Ile Lys
                180                 185                 190

Gln Leu Ile Glu Leu Asp Tyr Leu Asn Pro Gly Ser Ile Arg Leu Phe
                195                 200                 205

Ile Leu Asp Glu Ala Asp Lys Leu Leu Glu Glu Gly Ser Phe Gln Glu
210                 215                 220

Gln Ile Asn Trp Ile Tyr Ser Ser Leu Pro Ala Ser Lys Gln Met Leu
225                 230                 235                 240

Ala Val Ser Ala Thr Tyr Pro Glu Phe Leu Ala Asn Ala Leu Thr Lys
                245                 250                 255

Tyr Met Arg Asp Pro Thr Phe Val Arg Leu Asn Ser Ser Asp Pro Ser
                260                 265                 270

Leu Ile Gly Leu Lys Gln Tyr Tyr Lys Val Val Asn Ser Tyr Pro Leu
                275                 280                 285

Ala His Lys Val Phe Glu Glu Lys Thr Gln His Leu Gln Glu Leu Phe
                290                 295                 300

Ser Arg Ile Pro Phe Asn Gln Ala Leu Val Phe Ser Asn Leu His Ser
305                 310                 315                 320

Arg Ala Gln His Leu Ala Asp Ile Leu Ser Ser Lys Gly Phe Pro Ala
                325                 330                 335

Glu Cys Ile Ser Gly Asn Met Asn Gln Asn Arg Leu Asp Ala Met
                340                 345                 350

Ala Lys Leu Lys His Phe His Cys Arg Val Leu Ile Ser Thr Asp Leu
                355                 360                 365

Thr Ser Arg Gly Ile Asp Ala Glu Lys Val Asn Leu Val Asn Leu
                370                 375                 380

Asp Val Pro Leu Asp Trp Glu Thr Tyr Met His Arg Ile Gly Arg Ala
385                 390                 395                 400

Gly Arg Phe Gly Thr Leu Gly Leu Thr Val Thr Tyr Cys Cys Arg Gly
                405                 410                 415
```

```
Glu Glu Glu Asn Met Met Met Arg Ile Ala Gln Lys Cys Asn Ile Asn
            420                 425                 430
Leu Leu Pro Leu Pro Asp Pro Ile Pro Ser Gly Leu Met Glu Glu Cys
            435                 440                 445
Val Asp Trp Asp Val Glu Val Lys Ala Ala Val His Thr Tyr Gly Ile
450                 455                 460
Ala Ser Val Pro Asn Gln Pro Leu Lys Lys Gln Ile Gln Lys Ile Glu
465                 470                 475                 480
Arg Thr Leu Gln Ile Gln Lys Ala His Gly Asp His Met Ala Ser Ser
                485                 490                 495
Arg Asn Asn Ser Val Ser Gly Leu Ser Val Lys Ser Lys Asn Asn Thr
            500                 505                 510
Lys Gln Lys Leu Pro Val Lys Ser His Ser Glu Cys Gly Ile Ile Glu
            515                 520                 525
Lys Ala Thr Ser Pro Lys Glu Leu Gly Cys Asp Arg Gln Ser Glu Glu
530                 535                 540
Gln Met Lys Asn Ser Val Gln Thr Pro Val Glu Asn Ser Thr Asn Ser
545                 550                 555                 560
Gln His Gln Val Lys Glu Ala Leu Pro Val Ser Leu Pro Gln Ile Pro
                565                 570                 575
Cys Leu Ser Ser Phe Lys Ile His Gln Pro Tyr Thr Leu Thr Phe Ala
            580                 585                 590
Glu Leu Val Glu Asp Tyr Glu His Tyr Ile Lys Glu Gly Leu Glu Lys
            595                 600                 605
Pro Val Glu Ile Ile Arg His Tyr Thr Gly Pro Gly Asp Gln Thr Val
610                 615                 620
Asn Pro Gln Asn Gly Phe Val Arg Asn Lys Val Ile Glu Gln Arg Val
625                 630                 635                 640
Pro Val Leu Ala Ser Ser Gln Ser Gly Asp Ser Glu Ser Asp Ser
                645                 650                 655
Asp Ser Tyr Ser Ser Arg Thr Ser Ser Gln Ser Lys Gly Asn Lys Ser
            660                 665                 670
Tyr Leu Glu Gly Ser Ser Asp Asn Gln Leu Lys Asp Ser Glu Ser Thr
            675                 680                 685
Pro Val Asp Asp Arg Ile Ser Leu Glu Gln Pro Pro Asn Gly Ser Asp
690                 695                 700
Thr Pro Asn Pro Glu Lys Tyr Gln Glu Ser Pro Gly Ile Gln Met Lys
705                 710                 715                 720
Thr Arg Leu Lys Glu Gly Ala Ser Gln Arg Ala Lys Gln Ser Arg Arg
                725                 730                 735
Asn Leu Pro Arg Arg Ser Ser Phe Arg Leu Gln Thr Glu Ala Gln Glu
            740                 745                 750
Asp Asp Trp Tyr Asp Cys His Arg Glu Ile Arg Leu Ser Phe Ser Asp
            755                 760                 765
Thr Tyr Gln Asp Tyr Glu Glu Tyr Trp Arg Ala Tyr Tyr Arg Ala Trp
770                 775                 780
Gln Glu Tyr Tyr Ala Ala Ala Ser His Ser Tyr Tyr Trp Asn Ala Gln
785                 790                 795                 800
Arg His Pro Ser Trp Met Ala Ala Tyr His Met Asn Thr Ile Tyr Leu
                805                 810                 815
Gln Glu Met Met His Ser Asn Gln
            820

<210> SEQ ID NO 4
```

<211> LENGTH: 1058
<212> TYPE: PRT
<213> ORGANISM: Homo sapiens

<400> SEQUENCE: 4

```
Met Asp Leu Gly Pro Leu Asn Ile Cys Glu Glu Met Thr Ile Leu His
1               5                   10                  15

Gly Gly Phe Leu Leu Ala Glu Gln Leu Phe His Pro Lys Ala Leu Ala
            20                  25                  30

Glu Leu Thr Lys Ser Asp Trp Glu Arg Val Gly Arg Pro Ile Val Glu
        35                  40                  45

Ala Leu Arg Glu Ile Ser Ala Ala His Ser Gln Pro Phe Ala
    50                  55                  60

Trp Lys Lys Lys Ala Leu Ile Ile Ile Trp Ala Lys Val Leu Gln Pro
65                  70                  75                  80

His Pro Val Thr Pro Ser Asp Thr Glu Thr Arg Trp Gln Glu Asp Leu
                85                  90                  95

Phe Phe Ser Val Gly Asn Met Ile Pro Thr Ile Asn His Thr Ile Leu
            100                 105                 110

Phe Glu Leu Leu Lys Ser Leu Glu Ala Ser Gly Leu Phe Ile Gln Leu
        115                 120                 125

Leu Met Ala Leu Pro Thr Thr Ile Cys His Ala Glu Leu Glu Arg Phe
    130                 135                 140

Leu Glu His Val Thr Val Asp Thr Ser Ala Glu Asp Val Ala Phe Phe
145                 150                 155                 160

Leu Asp Ile Trp Trp Glu Val Met Lys His Lys Gly His Pro Gln Asp
                165                 170                 175

Pro Leu Leu Ser Gln Phe Ser Ala Met Ala His Lys Tyr Leu Pro Ala
            180                 185                 190

Leu Asp Glu Phe Pro His Pro Pro Lys Arg Leu Arg Ser Asp Pro Asp
        195                 200                 205

Ala Cys Pro Thr Met Pro Leu Leu Ala Met Leu Leu Arg Gly Leu Thr
    210                 215                 220

Gln Ile Gln Ser Arg Ile Leu Gly Pro Gly Arg Lys Cys Cys Ala Leu
225                 230                 235                 240

Ala Asn Leu Ala Asp Met Leu Thr Val Phe Ala Leu Thr Glu Asp Asp
                245                 250                 255

Pro Gln Glu Val Ser Ala Thr Val Tyr Leu Asp Lys Leu Ala Thr Val
            260                 265                 270

Ile Ser Val Trp Asn Ser Asp Thr Gln Asn Pro Tyr His Gln Gln Ala
        275                 280                 285

Leu Ala Glu Lys Val Lys Glu Ala Glu Arg Asp Val Ser Leu Thr Ser
    290                 295                 300

Leu Ala Lys Leu Pro Ser Glu Thr Ile Phe Val Gly Cys Glu Phe Leu
305                 310                 315                 320

His His Leu Leu Arg Glu Trp Gly Glu Glu Leu Gln Ala Val Leu Arg
                325                 330                 335

Ser Ser Gln Gly Thr Ser Tyr Asp Ser Tyr Arg Leu Cys Asp Ser Leu
            340                 345                 350

Thr Ser Phe Ser Gln Asn Ala Thr Leu Tyr Leu Asn Arg Thr Ser Leu
        355                 360                 365

Ser Lys Glu Asp Arg Gln Val Val Ser Glu Leu Ala Glu Cys Val Arg
    370                 375                 380

Asp Phe Leu Arg Lys Thr Ser Thr Val Leu Lys Asn Arg Ala Leu Glu
385                 390                 395                 400
```

```
Asp Ile Thr Ala Ser Ile Ala Met Ala Val Ile Gln Gln Lys Met Asp
            405                 410                 415
Arg His Met Glu Val Cys Tyr Ile Phe Ala Ser Glu Lys Lys Trp Ala
            420                 425                 430
Phe Ser Asp Glu Trp Val Ala Cys Leu Gly Ser Asn Arg Ala Leu Phe
            435                 440                 445
Arg Glu Pro Asp Leu Val Leu Arg Leu Glu Thr Val Ile Asp Val
        450                 455                 460
Ser Thr Ala Asp Arg Ala Ile Pro Glu Ser Gln Ile Arg Gln Val Ile
465                 470                 475                 480
His Leu Ile Leu Glu Cys Tyr Ala Asp Leu Ser Pro Gly Lys Asn
                485                 490                 495
Lys Val Leu Ala Gly Ile Leu Arg Ser Trp Gly Arg Lys Gly Leu Ser
                500                 505                 510
Glu Lys Leu Leu Ala Tyr Val Glu Gly Phe Gln Glu Asp Leu Asn Thr
        515                 520                 525
Thr Phe Asn Gln Leu Thr Gln Ser Ala Ser Glu Gln Gly Leu Ala Lys
        530                 535                 540
Ala Val Ala Ser Val Ala Arg Leu Val Ile Val His Pro Glu Val Thr
545                 550                 555                 560
Val Lys Lys Met Cys Ser Leu Ala Val Val Asn Leu Gly Thr His Lys
                565                 570                 575
Phe Leu Ala Gln Ile Leu Thr Ala Phe Pro Ala Leu Arg Phe Val Glu
                580                 585                 590
Val Gln Gly Pro Asn Ser Ser Ala Thr Phe Met Val Ser Cys Leu Lys
        595                 600                 605
Glu Thr Val Trp Met Lys Phe Ser Thr Pro Lys Glu Lys Gln Phe
        610                 615                 620
Leu Glu Leu Leu Asn Cys Leu Met Ser Pro Val Lys Pro Gln Gly Ile
625                 630                 635                 640
Pro Val Ala Ala Leu Leu Glu Pro Asp Glu Val Leu Lys Glu Phe Val
                645                 650                 655
Leu Pro Phe Leu Arg Leu Asp Val Glu Glu Val Asp Leu Ser Leu Arg
                660                 665                 670
Ile Phe Ile Gln Thr Leu Glu Ala Asn Ala Cys Arg Glu Glu Tyr Trp
                675                 680                 685
Leu Gln Thr Cys Ser Pro Phe Pro Leu Leu Phe Ser Leu Cys Gln Leu
        690                 695                 700
Leu Asp Arg Phe Ser Lys Tyr Trp Pro Leu Pro Lys Glu Lys Arg Cys
705                 710                 715                 720
Leu Ser Leu Asp Arg Lys Asp Leu Ala Ile His Ile Leu Glu Leu Leu
                725                 730                 735
Cys Glu Ile Val Ser Ala Asn Ala Glu Thr Phe Ser Pro Asp Val Trp
                740                 745                 750
Ile Lys Ser Leu Ser Trp Leu His Arg Lys Leu Glu Gln Leu Asp Trp
                755                 760                 765
Thr Val Gly Leu Arg Leu Lys Ser Phe Phe Glu Gly His Phe Lys Cys
        770                 775                 780
Glu Val Pro Ala Thr Leu Phe Glu Ile Cys Lys Leu Ser Glu Asp Glu
785                 790                 795                 800
Trp Thr Ser Gln Ala His Pro Gly Tyr Gly Ala Gly Thr Gly Leu Leu
                805                 810                 815
Ala Trp Met Glu Cys Cys Cys Val Ser Ser Gly Ile Ser Glu Arg Met
```

```
                      820                 825                 830
Leu Ser Leu Leu Val Val Asp Val Gly Asn Pro Glu Glu Val Arg Leu
        835                 840                 845

Phe Ser Lys Gly Phe Leu Val Ala Leu Val Gln Val Met Pro Trp Cys
    850                 855                 860

Ser Pro Gln Glu Trp Gln Arg Leu His Gln Leu Thr Arg Arg Leu Leu
865                 870                 875                 880

Glu Lys Gln Leu Leu His Val Pro Tyr Ser Leu Glu Tyr Ile Gln Phe
                885                 890                 895

Val Pro Leu Leu Asn Leu Lys Pro Phe Ala Gln Glu Leu Gln Leu Ser
            900                 905                 910

Val Leu Phe Leu Arg Thr Phe Gln Phe Leu Cys Ser His Ser Cys Arg
        915                 920                 925

Asn Trp Leu Pro Leu Glu Gly Trp Asn His Val Val Lys Leu Leu Cys
    930                 935                 940

Gly Ser Leu Thr Arg Leu Leu Asp Ser Val Arg Ala Ile Gln Ala Ala
945                 950                 955                 960

Gly Pro Trp Val Gln Gly Pro Glu Gln Asp Leu Thr Gln Glu Ala Leu
                965                 970                 975

Phe Val Tyr Thr Gln Val Phe Cys His Ala Leu His Ile Met Ala Met
            980                 985                 990

Leu His Pro Glu Val Cys Glu Pro Leu Tyr Val Leu Ala Leu Glu Thr
        995                 1000                1005

Leu Thr Cys Tyr Glu Thr Leu Ser Lys Thr Asn Pro Ser Val Ser
    1010                1015                1020

Ser Leu Leu Gln Arg Ala His Glu Gln Arg Phe Leu Lys Ser Ile
    1025                1030                1035

Ala Glu Gly Ile Gly Pro Glu Glu Arg Arg Gln Thr Leu Leu Gln
    1040                1045                1050

Lys Met Ser Ser Phe
    1055

<210> SEQ ID NO 5
<211> LENGTH: 1508
<212> TYPE: PRT
<213> ORGANISM: Homo sapiens

<400> SEQUENCE: 5

Met Gly Gln Glu Pro Arg Thr Leu Pro Pro Ser Pro Asn Trp Tyr Cys
1               5                   10                  15

Ala Arg Cys Ser Asp Ala Val Pro Gly Gly Leu Phe Gly Phe Ala Ala
            20                  25                  30

Arg Thr Ser Val Phe Leu Val Arg Val Gly Pro Ala Gly Glu Gly Ser
        35                  40                  45

Pro Gly Thr Pro Pro Phe Arg Val Ile Gly Glu Leu Val Gly His Thr
    50                  55                  60

Glu Arg Val Ser Gly Phe Thr Phe Ser His His Pro Gly Gln Tyr Asn
65                  70                  75                  80

Leu Cys Ala Thr Ser Ser Asp Asp Gly Thr Val Lys Ile Trp Asp Val
                85                  90                  95

Glu Thr Lys Thr Val Val Thr Glu His Ala Leu His Gln His Thr Ile
            100                 105                 110

Ser Thr Leu His Trp Ser Pro Arg Val Lys Asp Leu Ile Val Ser Gly
        115                 120                 125

Asp Glu Lys Gly Val Val Phe Cys Tyr Trp Phe Asn Arg Asn Asp Ser
```

```
            130                 135                 140
Gln His Leu Phe Ile Glu Pro Arg Thr Ile Phe Cys Leu Thr Cys Ser
145                 150                 155                 160

Pro His His Glu Asp Leu Val Ala Ile Gly Tyr Lys Asp Gly Ile Val
            165                 170                 175

Val Ile Ile Asp Ile Ser Lys Lys Gly Glu Val Ile His Arg Leu Arg
                180                 185                 190

Gly His Asp Asp Glu Ile His Ser Ile Ala Trp Cys Pro Leu Pro Gly
            195                 200                 205

Glu Asp Cys Leu Ser Ile Asn Gln Glu Glu Thr Ser Glu Glu Ala Glu
210                 215                 220

Ile Thr Asn Gly Asn Ala Val Ala Gln Ala Pro Val Thr Lys Gly Cys
225                 230                 235                 240

Tyr Leu Ala Thr Gly Ser Lys Asp Gln Thr Ile Arg Ile Trp Ser Cys
                245                 250                 255

Ser Arg Gly Arg Gly Val Met Ile Leu Lys Leu Pro Phe Leu Lys Arg
            260                 265                 270

Arg Gly Gly Ile Asp Pro Thr Val Lys Glu Arg Leu Trp Leu Thr
        275                 280                 285

Leu His Trp Pro Ser Asn Gln Pro Thr Gln Leu Val Ser Ser Cys Phe
290                 295                 300

Gly Gly Glu Leu Leu Gln Trp Asp Leu Thr Gln Ser Trp Arg Arg Lys
305                 310                 315                 320

Tyr Thr Leu Phe Ser Ala Ser Ser Glu Gly Gln Asn His Ser Arg Ile
                325                 330                 335

Val Phe Asn Leu Cys Pro Leu Gln Thr Glu Asp Asp Lys Gln Leu Leu
            340                 345                 350

Leu Ser Thr Ser Met Asp Arg Asp Val Lys Cys Trp Asp Ile Ala Thr
        355                 360                 365

Leu Glu Cys Ser Trp Thr Leu Pro Ser Leu Gly Gly Phe Ala Tyr Ser
        370                 375                 380

Leu Ala Phe Ser Ser Val Asp Ile Gly Ser Leu Ala Ile Gly Val Gly
385                 390                 395                 400

Asp Gly Met Ile Arg Val Trp Asn Thr Leu Ser Ile Lys Asn Asn Tyr
                405                 410                 415

Asp Val Lys Asn Phe Trp Gln Gly Val Lys Ser Lys Val Thr Ala Leu
            420                 425                 430

Cys Trp His Pro Thr Lys Glu Gly Cys Leu Ala Phe Gly Thr Asp Asp
        435                 440                 445

Gly Lys Val Gly Leu Tyr Asp Thr Tyr Ser Asn Lys Pro Pro Gln Ile
    450                 455                 460

Ser Ser Thr Tyr His Lys Lys Thr Val Tyr Thr Leu Ala Trp Gly Pro
465                 470                 475                 480

Pro Val Pro Pro Met Ser Leu Gly Gly Glu Gly Asp Arg Pro Ser Leu
            485                 490                 495

Ala Leu Tyr Ser Cys Gly Gly Glu Gly Ile Val Leu Gln His Asn Pro
        500                 505                 510

Trp Lys Leu Ser Gly Glu Ala Phe Asp Ile Asn Lys Leu Ile Arg Asp
        515                 520                 525

Thr Asn Ser Ile Lys Tyr Lys Leu Pro Val His Thr Glu Ile Ser Trp
    530                 535                 540

Lys Ala Asp Gly Lys Ile Met Ala Leu Gly Asn Glu Asp Gly Ser Ile
545                 550                 555                 560
```

```
Glu Ile Phe Gln Ile Pro Asn Leu Lys Leu Ile Cys Thr Ile Gln Gln
                565                 570                 575

His His Lys Leu Val Asn Thr Ile Ser Trp His His Glu His Gly Ser
            580                 585                 590

Gln Pro Glu Leu Ser Tyr Leu Met Ala Ser Gly Ser Asn Asn Ala Val
        595                 600                 605

Ile Tyr Val His Asn Leu Lys Thr Val Ile Glu Ser Ser Pro Glu Ser
    610                 615                 620

Pro Val Thr Ile Thr Glu Pro Tyr Arg Thr Leu Ser Gly His Thr Ala
625                 630                 635                 640

Lys Ile Thr Ser Val Ala Trp Ser Pro His His Asp Gly Arg Leu Val
                645                 650                 655

Ser Ala Ser Tyr Asp Gly Thr Ala Gln Val Trp Asp Ala Leu Arg Glu
            660                 665                 670

Glu Pro Leu Cys Asn Phe Arg Gly His Arg Gly Arg Leu Leu Cys Val
        675                 680                 685

Ala Trp Ser Pro Leu Asp Pro Asp Cys Ile Tyr Ser Gly Ala Asp Asp
    690                 695                 700

Phe Cys Val His Lys Trp Leu Thr Ser Met Gln Asp His Ser Arg Pro
705                 710                 715                 720

Pro Gln Gly Lys Lys Ser Ile Glu Leu Glu Lys Lys Arg Leu Ser Gln
                725                 730                 735

Pro Lys Ala Lys Pro Lys Lys Lys Lys Pro Thr Leu Arg Thr Pro
            740                 745                 750

Val Lys Leu Glu Ser Ile Asp Gly Asn Glu Glu Ser Met Lys Glu
        755                 760                 765

Asn Ser Gly Pro Val Glu Asn Gly Val Ser Asp Gln Glu Gly Glu Glu
770                 775                 780

Gln Ala Arg Glu Pro Glu Leu Pro Cys Gly Leu Ala Pro Ala Val Ser
785                 790                 795                 800

Arg Glu Pro Val Ile Cys Thr Pro Val Ser Ser Gly Phe Glu Lys Ser
                805                 810                 815

Lys Val Thr Ile Asn Asn Lys Val Ile Leu Leu Lys Lys Glu Pro Pro
            820                 825                 830

Lys Glu Lys Pro Glu Thr Leu Ile Lys Lys Arg Lys Ala Arg Ser Leu
        835                 840                 845

Leu Pro Leu Ser Thr Ser Leu Asp His Arg Ser Lys Glu Glu Leu His
    850                 855                 860

Gln Asp Cys Leu Val Leu Ala Thr Ala Lys His Ser Arg Glu Leu Asn
865                 870                 875                 880

Glu Asp Val Ser Ala Asp Val Glu Glu Arg Phe His Leu Gly Leu Phe
                885                 890                 895

Thr Asp Arg Ala Thr Leu Tyr Arg Met Ile Asp Ile Glu Gly Lys Gly
            900                 905                 910

His Leu Glu Asn Gly His Pro Glu Leu Phe His Gln Leu Met Leu Trp
        915                 920                 925

Lys Gly Asp Leu Lys Gly Val Leu Gln Thr Ala Ala Glu Arg Gly Glu
    930                 935                 940

Leu Thr Asp Asn Leu Val Ala Met Ala Pro Ala Ala Gly Tyr His Val
945                 950                 955                 960

Trp Leu Trp Ala Val Glu Ala Phe Ala Lys Gln Leu Cys Phe Gln Asp
                965                 970                 975

Gln Tyr Val Lys Ala Ala Ser His Leu Leu Ser Ile His Lys Val Tyr
            980                 985                 990
```

```
Glu Ala Val Glu Leu Leu Lys Ser Asn His Phe Tyr Arg Glu Ala Ile
        995                 1000                1005

Ala Ile Ala Lys Ala Arg Leu Arg Pro Glu Asp Pro Val Leu Lys
    1010                1015                1020

Asp Leu Tyr Leu Ser Trp Gly Thr Val Leu Glu Arg Asp Gly His
    1025                1030                1035

Tyr Ala Val Ala Ala Lys Cys Tyr Leu Gly Ala Thr Cys Ala Tyr
    1040                1045                1050

Asp Ala Ala Lys Val Leu Ala Lys Lys Gly Asp Ala Ala Ser Leu
    1055                1060                1065

Arg Thr Ala Ala Glu Leu Ala Ala Ile Val Gly Glu Asp Glu Leu
    1070                1075                1080

Ser Ala Ser Leu Ala Leu Arg Cys Ala Gln Glu Leu Leu Leu Ala
    1085                1090                1095

Asn Asn Trp Val Gly Ala Gln Ala Leu Gln Leu His Glu Ser
    1100                1105                1110

Leu Gln Gly Gln Arg Leu Val Phe Cys Leu Leu Glu Leu Leu Ser
    1115                1120                1125

Arg His Leu Glu Glu Lys Gln Leu Ser Glu Gly Lys Ser Ser Ser
    1130                1135                1140

Ser Tyr His Thr Trp Asn Thr Gly Thr Glu Gly Pro Phe Val Glu
    1145                1150                1155

Arg Val Thr Ala Val Trp Lys Ser Ile Phe Ser Leu Asp Thr Pro
    1160                1165                1170

Glu Gln Tyr Gln Glu Ala Phe Gln Lys Leu Gln Asn Ile Lys Tyr
    1175                1180                1185

Pro Ser Ala Thr Asn Asn Thr Pro Ala Lys Gln Leu Leu Leu His
    1190                1195                1200

Ile Cys His Asp Leu Thr Leu Ala Val Leu Ser Gln Gln Met Ala
    1205                1210                1215

Ser Trp Asp Glu Ala Val Gln Ala Leu Leu Arg Ala Val Val Arg
    1220                1225                1230

Ser Tyr Asp Ser Gly Ser Phe Thr Ile Met Gln Glu Val Tyr Ser
    1235                1240                1245

Ala Phe Leu Pro Asp Gly Cys Asp His Leu Arg Asp Lys Leu Gly
    1250                1255                1260

Asp His Gln Ser Pro Ala Thr Pro Ala Phe Lys Ser Leu Glu Ala
    1265                1270                1275

Phe Phe Leu Tyr Gly Arg Leu Tyr Glu Phe Trp Trp Ser Leu Ser
    1280                1285                1290

Arg Pro Cys Pro Asn Ser Ser Val Trp Val Arg Ala Gly His Arg
    1295                1300                1305

Thr Leu Ser Val Glu Pro Ser Gln Gln Leu Asp Thr Ala Ser Thr
    1310                1315                1320

Glu Glu Thr Asp Pro Glu Thr Ser Gln Pro Glu Pro Asn Arg Pro
    1325                1330                1335

Ser Glu Leu Asp Leu Arg Leu Thr Glu Glu Gly Glu Arg Met Leu
    1340                1345                1350

Ser Thr Phe Lys Glu Leu Phe Ser Glu Lys His Ala Ser Leu Gln
    1355                1360                1365

Asn Ser Gln Arg Thr Val Ala Glu Val Gln Glu Thr Leu Ala Glu
    1370                1375                1380

Met Ile Arg Gln His Gln Lys Ser Gln Leu Cys Lys Ser Thr Ala
```

```
                   1385                1390                1395

Asn Gly Pro Asp Lys Asn Glu Pro Glu Val Glu Ala Glu Gln Pro
        1400                1405                1410

Leu Cys Ser Ser Gln Ser Gln Cys Lys Glu Glu Lys Asn Glu Pro
        1415                1420                1425

Leu Ser Leu Pro Glu Leu Thr Lys Arg Leu Thr Glu Ala Asn Gln
        1430                1435                1440

Arg Met Ala Lys Phe Pro Glu Ser Ile Lys Ala Trp Pro Phe Pro
        1445                1450                1455

Asp Val Leu Glu Cys Cys Leu Val Leu Leu Ile Arg Ser His
        1460                1465                1470

Phe Pro Gly Cys Leu Ala Gln Glu Met Gln Gln Ala Gln Glu
        1475                1480                1485

Leu Leu Gln Lys Tyr Gly Asn Thr Lys Thr Tyr Arg Arg His Cys
        1490                1495                1500

Gln Thr Phe Cys Met
        1505

<210> SEQ ID NO 6
<211> LENGTH: 167
<212> TYPE: PRT
<213> ORGANISM: Homo sapiens

<400> SEQUENCE: 6

Met Ser Glu Trp Met Lys Lys Gly Pro Leu Glu Trp Gln Asp Tyr Ile
1               5                   10                  15

Tyr Lys Glu Val Arg Val Thr Ala Ser Glu Lys Asn Glu Tyr Lys Gly
                20                  25                  30

Trp Val Leu Thr Thr Asp Pro Val Ser Ala Asn Ile Val Leu Val Asn
                35                  40                  45

Phe Leu Glu Asp Gly Ser Met Ser Val Thr Gly Ile Met Gly His Ala
        50                  55                  60

Val Gln Thr Val Glu Thr Met Asn Glu Gly Asp His Arg Val Arg Glu
65                  70                  75                  80

Lys Leu Met His Leu Phe Thr Ser Gly Asp Cys Lys Ala Tyr Ser Pro
                85                  90                  95

Glu Asp Leu Glu Glu Arg Lys Asn Ser Leu Lys Lys Trp Leu Glu Lys
                100                 105                 110

Asn His Ile Pro Ile Thr Glu Gln Gly Asp Ala Pro Arg Thr Leu Cys
                115                 120                 125

Val Ala Gly Val Leu Thr Ile Asp Pro Pro Tyr Gly Pro Glu Asn Cys
        130                 135                 140

Ser Ser Ser Asn Glu Ile Ile Leu Ser Arg Val Gln Asp Leu Ile Glu
145                 150                 155                 160

Gly His Leu Thr Ala Ser Gln
                165

<210> SEQ ID NO 7
<211> LENGTH: 131
<212> TYPE: PRT
<213> ORGANISM: Homo sapiens

<400> SEQUENCE: 7

Met Gln Thr Pro Val Asn Ile Pro Val Pro Val Leu Arg Leu Pro Arg
1               5                   10                  15

Gly Pro Asp Gly Phe Ser Arg Gly Phe Ala Pro Asp Gly Arg Arg Ala
                20                  25                  30
```

```
Pro Leu Arg Pro Glu Val Pro Glu Ile Gln Glu Cys Pro Ile Ala Gln
        35                  40                  45

Glu Ser Leu Glu Ser Gln Gln Arg Ala Arg Ala Ala Leu Arg Glu
 50                  55                  60

Arg Tyr Leu Arg Ser Leu Leu Ala Met Val Gly His Gln Val Ser Phe
 65                  70                  75                  80

Thr Leu His Glu Gly Val Arg Val Ala Ala His Phe Gly Ala Thr Asp
                 85                  90                  95

Leu Asp Val Ala Asn Phe Tyr Val Ser Gln Leu Gln Thr Pro Ile Gly
                100                 105                 110

Val Gln Ala Glu Ala Leu Leu Arg Cys Ser Asp Ile Ile Ser Tyr Thr
                115                 120                 125

Phe Lys Pro
    130

<210> SEQ ID NO 8
<211> LENGTH: 19
<212> TYPE: RNA
<213> ORGANISM: Homo sapiens

<400> SEQUENCE: 8
gaagaauacu gcagcuucc                                                  19

<210> SEQ ID NO 9
<211> LENGTH: 19
<212> TYPE: RNA
<213> ORGANISM: Homo sapiens

<400> SEQUENCE: 9
gcagcucaau guccagaug                                                  19

<210> SEQ ID NO 10
<211> LENGTH: 19
<212> TYPE: RNA
<213> ORGANISM: Homo sapiens

<400> SEQUENCE: 10
ggcuuagagu gucaugucu                                                  19

<210> SEQ ID NO 11
<211> LENGTH: 19
<212> TYPE: RNA
<213> ORGANISM: Homo sapiens

<400> SEQUENCE: 11
acuccccagu gagaccauu                                                  19

<210> SEQ ID NO 12
<211> LENGTH: 19
<212> TYPE: RNA
<213> ORGANISM: Homo sapiens

<400> SEQUENCE: 12
gcauaguggu gauaauuga                                                  19

<210> SEQ ID NO 13
<211> LENGTH: 21
<212> TYPE: RNA
<213> ORGANISM: Homo sapiens

<400> SEQUENCE: 13
```

```
aacuacagac ccagucucug c                                              21

<210> SEQ ID NO 14
<211> LENGTH: 19
<212> TYPE: RNA
<213> ORGANISM: Homo sapiens

<400> SEQUENCE: 14
cccggaccac aacgcucug                                                 19
```

METHOD FOR TESTING OR SCREENING PROTEIN SYNTHESIS INHIBITORS

CROSS-REFERENCE TO RELATED APPLICATIONS

This is a national stage application of PCT patent application PCT/US2008/006972, filed Jun. 4, 2008, that claims the benefit of priority from U.S. Provisional Application 60/924,883, filed Jun. 4, 2007, both of which are incorporated by reference herein in their entirety.

FIELD OF INVENTION

This invention provides: methods, kits, and systems for testing protein synthesis inhibitors.

BACKGROUND OF THE INVENTION

Translation is the RNA directed synthesis of polypeptides. This process requires all three classes of RNA. Although the chemistry of peptide bond formation is relatively simple, the processes leading to the ability to form a peptide bond are exceedingly complex. The template for correct addition of individual amino acids is the mRNA, yet both tRNAs and rRNAs are involved in the process. The tRNAs carry activated amino acids into the ribosome which is composed of rRNA and ribosomal proteins. The ribosome is associated with the mRNA ensuring correct access of activated tRNAs and containing the necessary enzymatic activities to catalyze peptide bond formation.

Regulation of this information pathway can be achieved at a number of levels, including the modulation of translation factor levels or activity, ribosome biogenesis, and small molecule/RNA interactions. Small molecule ligands that inhibit the process of translation provide exquisite insight into ribosome function and translation factor activity in both prokaryotes and eukaryotes.

Inhibitors targeting a specific step of protein synthesis enable dissection of the translation pathway by allowing the characterization of events leading to the assembly of active polysomes, trapping intermediates of the initiation and elongation cycle, and providing insight into the molecular functions of protein factors.

Deregulation of protein synthesis is a major contributor in cancer initiation and metastatic progression. Overexpression of some initiation factors can lead to malignant transformation, whereas down-regulation of these same factors can suppress the transformed phenotype. In cancers components of the translation apparatus are overexpressed or mutated. For example, the tumor suppressor gene product pRB directly impacts on the translation process by affecting the levels of ribosomes. Furthermore, key components of anti-apoptotic pathways are translationally regulated.

Thus, protein synthesis represents a valid target for chemotherapeutic intervention. Few inhibitors of protein synthesis have been tested in clinical trials, with some of these demonstrating encouraging therapeutic effects. Presumably, a therapeutic index is achieved due to the higher requirement of transformed cells for protein synthesis, as well as translation regulation of some of the proteins involved in cancer progression. Unfortunately, dose-limiting secondary effects have hampered further development of many of these compounds.

SUMMARY OF THE INVENTION

This invention provides, in one embodiment, a method for testing a candidate compound for an ability to inhibit protein synthesis in a cell, comprising the steps of: contacting a cell with a candidate compound; and measuring the level of a SMN complex component in the cytoplasm of a cell, the nucleus of a cell, or a combination thereof, whereby, if a candidate compound increases the amount of the SMN complex component in the nucleus, decreases the amount of the SMN complex component in the cytoplasm, or a combination thereof, then the compound exhibits an ability to inhibit protein synthesis.

In another embodiment, the present invention provides a method for screening or testing a library of compounds for ability to treat a disease associated with protein synthesis inhibition, wherein the disease is selected from a viral disease, cancer, or a neurodegenerative disease, comprising the steps of: contacting a cell with a test compound, and measuring the level of an SMN complex component relocalization from the cytoplasm to the nucleus, whereby, if the test compound causes relocalization of a SMN complex component from the cytoplasm to the nucleus, then the test compound has an ability to treat the disease associated with protein synthesis inhibition.

In another embodiment, the present invention provides a kit for screening or testing potential protein synthesis inhibitors in a cell, comprising a reagent for measuring a level of an SMN complex component in the nucleus of the cell, the cytoplasm of the cell, or a combination thereof.

In another embodiment, the present invention provides a system for screening or testing protein synthesis inhibitors in a cell, comprising a kit for measuring protein synthesis inhibitors in a cell, comprising an SMN complex component relocalization measuring reagents.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 2A shows immunostaining of SMN in DMSO-treated cells. FIG. 2B shows immunostaining of SMN in cells treated for 4 hours with a compound from the library that was identified as having a significant change in SMN sub-cellular distribution.

FIG. 5A shows immunostaining of SMN in DMSO treated cells (control) and in cells treated with 2 µM TSA, 7.5 mM VPA, 8 µM scriptaid, 10 µM HDAC inhibitor 1 and 5 µM apicidin for 24 hours. FIG. 5B shows immunostaining of SMN in HeLa cells treated with 2-10 mM VPA. FIG. 5C shows immunostaining of Gemins 2, 3, 5, and 6 in control cells (upper panel) and in cells treated for 24 hrs with 10 mM VPA (lower panel).

FIG. 6a is immunostaining of SMN in control HeLa cells (left panel) and in cells treated with an inactive analogue of cycloheximide, cycloheximide-N-ethylethanoate (CHX-N) at 10 µM. FIG. 6b is immunostaining of SMN showing nuclear accumulation in cells treated with 10 µM emetine, 10 µM puromycin, 10 µM thapsigargin and 10 µg/ml tunicamycin, as depicted on the panels.

DETAILED DESCRIPTION OF THE INVENTION

Figure 1:
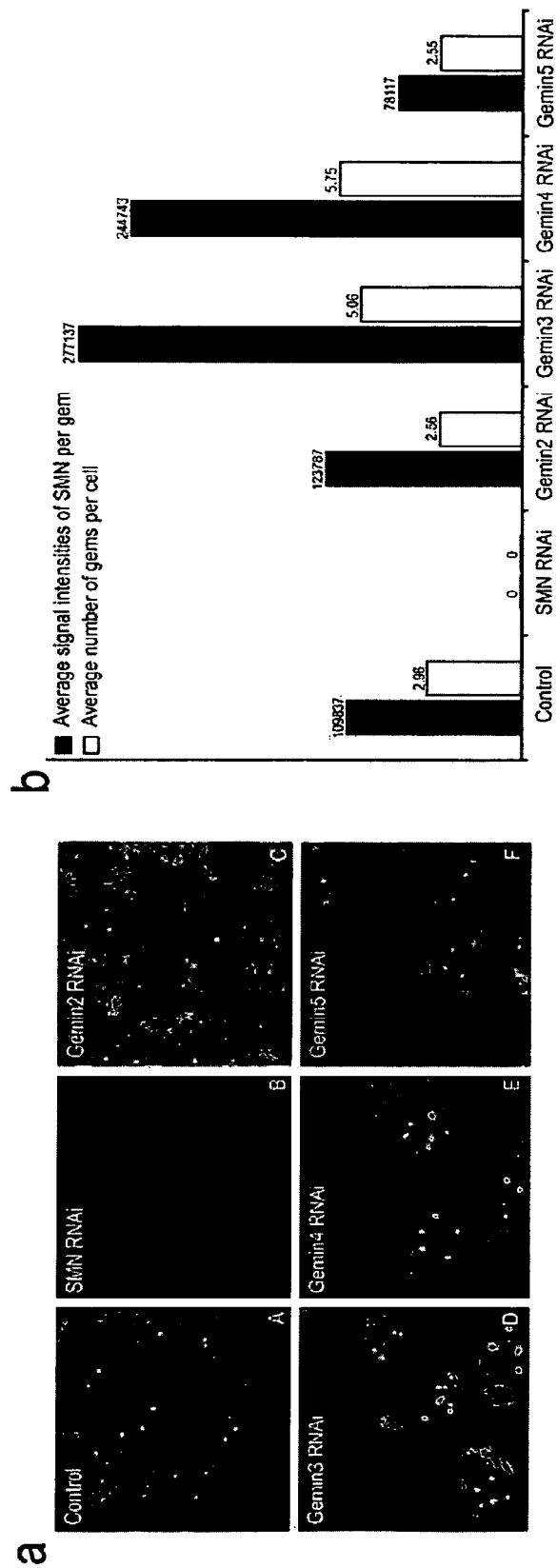
FIG. 1A shows an immunostaining micrograph [×40] of SMN following treatment with RNAi of a non-targeting siRNA (A), following RNAi of SMN (B), RNAi of Gemin2 (C), RNAi of Gemin3 (D), RNAi of Gemin4 (E) and RNAi of Gemin5 (F).
FIG. 1B depicts a bar graph which represents quantitation of the average anti-SMN (2B1) antibody signal intensities per Gem (black bars) and the average numbers of Gems per cell (white bars) of the images shown in FIG. 1A.

In one embodiment, the present invention provides a method for testing an ability of a compound to inhibit protein synthesis, comprising the steps of contacting a cell with the compound and measuring the level of SMN complex in the cytoplasm of the cell, the nucleus of the cell, or a combination thereof, whereby, if the compound increases the amount of the SMN complex in the nucleus, decreases the amount of the SMN complex in the cytoplasm, or a combination thereof, then the compound exhibits an ability to inhibit protein synthesis.

In another embodiment, relocalization of a SMN complex component from the cytoplasm to the nucleus is measured. In another embodiment, calculating a change in distribution of an SMN complex component in the cytoplasm and the nucleus of a cell comprises measuring the level of relocalization of a SMN complex component from the cytoplasm to the nucleus. In another embodiment, calculating a change in distribution of an SMN complex component in the cytoplasm and the nucleus of a cell comprises measuring the distribution of an SMN complex component in the cytoplasm and the nucleus in a cell. Each possibility represents a separate embodiment of the present invention.

In one embodiment, the present invention provides a method for screening or testing a library of compounds for an inhibitor of protein synthesis, comprising the steps of contacting a plurality of cells or cell samples with potential inhibitors of protein synthesis, and measuring the level of SMN complex in the cytoplasm of the cell, the nucleus of the cell, or a combination thereof, whereby, if a compound in the library increases the amount of the SMN complex in the nucleus, decreases the amount of the SMN complex in the cytoplasm, or a combination thereof, then the compound exhibits an ability to inhibit protein synthesis.

In another embodiment, each of the cells or cell samples is contacted with a different compound from the library. In another embodiment, relocalization of a SMN complex component from the cytoplasm to the nucleus is measured. In another embodiment, measuring relocalization of a SMN complex component from the cytoplasm to the nucleus comprises calculating a change in distribution of an SMN complex component in the cytoplasm and the nucleus of a cell. In another embodiment, calculating a change in distribution of an SMN complex component in the cytoplasm and the nucleus of a cell comprises measuring the distribution of an SMN complex component in the cytoplasm and the nucleus in a cell. Each possibility represents a separate embodiment of the present invention.

In another embodiment, the SMN complex component is a Gem. In another embodiment, Gems are discrete SMN complex bodies in the nucleus. In another embodiment, "SMN complex components" comprise, in addition to SMN, other proteins termed "Gemins."

In another embodiment, the Gemin protein is Gemin1 protein. In another embodiment, the sequence of the Gemin1 protein comprises the sequence:

(SEQ. ID NO: 1)
MAMSSGGSGGGVPEQEDSVLFRRGTGQSDDSDIWDDTALIKAYDKAVASF

KHALKNGDICETSGKPKTTPKRKPAKKNKSQKKNTAASLQQWKVGDKCSA

IWSEDGCIYPATIASIDFKRETCVVVYTGYGNREEQNLSDLLSPICEVAN

NIEQNAQENENESQVSTDESENSRSPGNKSDNIKPKSAPWNSFLPPPPPM

PGPRLGPGKPGLKFNGPPPPPPPPPHLLSCWLPPFPSGPPIIPPPPPIC

PDSLDDADALGSMLISWYMSGYHTGYYMGFRQNQKEGRCSHSLN.

In another embodiment, the Gemin1 protein of the present invention comprises an amino acid sequence homologous to SEQ. ID. NO: 1. In another embodiment, the Gemin 1 protein is a Homo sapiens Gemin1 protein. In another embodiment, the Gemin1 protein is from a non-human species. Each possibility represents a separate embodiment of the present invention.

In another embodiment, the Gemin protein is Gemin2 protein. In another embodiment, the sequence of the Gemin2 protein comprises the sequence:

(SEQ ID NO: 2)
MRRAELAGLKTMAWVPAESAVEELMPRLLPVEPCDLTEGFDPSVPPRTPQ

EYLRRVQIEAAQCPDVVVAQIDPKKLKRKQSVNISLSGCQPAPEGYSPTL

QWQQQQVAQFSTVRQNVNKHRSHWKSQQLDSNVTMPKSEDEEGWKKFCLG

EKLCADGAVGPATNESPGIDYVQIGFPPLLSIVSRMNQATVTSVLEYLSN

WFGERDETPELGRWLYALLACLEKPLLPEAHSLIRQLARRCSEVRLLVDS

KDDERVPALNLLICLVSRYFDQRDLADEPS.

In another embodiment, the Gemin2 protein of the present invention comprises an amino acid sequence homologous to SEQ. ID. NO: 2. In another embodiment, the Gemin2 protein is a Homo sapiens Gemin2 protein. In another embodiment, the Gemin2 protein is from a non-human species. Each possibility represents a separate embodiment of the present invention.

In another embodiment, the Gemin protein is Gemin3 protein. In another embodiment, the sequence of the Gemin3 protein comprises the sequence:

```
                                         (SEQ. ID NO: 3)
MAAAFEASGALAAVATAMPAEHVAVQVPAPEPTPGPVRILRTAQDLSSPR

TRTGDVLLAEPADFESLLLSRPVLEGLRAAGFERPSPVQLKAIPLGRCGL

DLIVQAKSGTGKTCVFSTIALDSLVLENLSTQILILAPTREIAVQIHSVI

TAIGIKMEGLECHVFIGGTPLSQDKTRLKKCHIAVGSPGRIKQLIELDYL

NPGSIRLFILDEADKLLEEGSFQEQINWIYSSLPASKQMLAVSATYPEFL

ANALTKYMRDPTFVRLNSSDPSLIGLKQYYKVVNSYPLAHKVFEEKTQHL

QELFSRIPFNQALVFSNLHSRAQHLADILSSKGFPAECISGNMNQNQRLD

AMAKLKHFHCRVLISTDLTSRGIDAEKVNLVVNLDVPLDWETYMHRIGRA

GRFGTLGLTVTYCCRGEEENMMMRIAQKCNINLLPLPDPIPSGLMEECVD

WDVEVKAAVHTYGIASVPNQPLKKQIQKIERTLQIQKAHGDHMASSRNNS

VSGLSVKSKNNTKQKLPVKSHSECGIIEKATSPKELGCDRQSEEQMKNSV

QTPVENSTNSQHQVKEALPVSLPQIPCLSSFKIHQPYTLTFAELVEDYEH

YIKEGLEKPVEIIRHYTGPGDQTVNPQNGFVRNKVIEQRVPVLASSSQSG

DSESDSDSYSSRTSSQSKGNKSYLEGSSDNQLKDSESTPVDDRISLEQPP

NGSDTPNPEKYQESPGIQMKTRLKEGASQRAKQSRRNLPRRSSFRLQTEA

QEDDWYDCHREIRLSFSDTYQDYEEYWRAYYRAWQEYYAAASHSYYWNAQ

RHPSWMAAYHMNTIYLQEMMHSNQ.
```

In another embodiment, the Gemin3 protein of the present invention comprises an amino acid sequence homologous to SEQ. ID. NO: 3. In another embodiment, the Gemin3 protein is a Homo sapiens Gemin3 protein. In another embodiment, the Gemin3 protein is from a non-human species. Each possibility represents a separate embodiment of the present invention.

In another embodiment, the Gemin protein is Gemin4 protein. In another embodiment, the sequence of the Gemin4 protein comprises the sequence:

```
                                         (SEQ. ID NO: 4)
MDLGPLNICEEMTILHGGFLLAEQLFHPKALAELTKSDWERVGRPIVEAL

REISSAAAHSQPFAWKKKALIIIWAKVLQPHPVTPSDTETRWQEDLFFSV

GNMIPTINHTILFELLKSLEASGLFIQLLMALPTTICHAELERFLEHVTV

DTSAEDVAFFLDIWWEVMKHKGHPQDPLLSQFSAMAHKYLPALDEFPHPP

KRLRSDPDACPTMPLLAMLLRGLTQIQSRILGPGRKCCALANLADMLTVF

ALTEDDPQEVSATVYLDKLATVISVWNSDTQNPYHQQALAEKVKEAERDV

SLTSLAKLPSETIFVGCEFLHHLLREWGEELQAVLRSSQGTSYDSYRLCD

SLTSFSQNATLYLNRTSLSKEDRQVVSELAECVRDFLRKTSTVLKNRALE

DITASIAMAVIQQKMDRHMEVCYIFASEKKWAFSDEWVACLGSNRALFRE

PDLVLRLLETVIDVSTADRAIPESQIRQVIHLILECYADLSLPGKNKVLA

GILRSWGRKGLSEKLLAYVEGFQEDLNTTFNQLTQSASEQGLAKAVASVA

RLVIVHPEVTVKKMCSLAVVNLGTHKFLAQILTAFPALRFVEVQGPNSSA

TFMVSCLKETVWMKFSTPKEEKQFLELLNCLMSPVKPQGIPVAALLEPDE

VLKEFVLPFLRLDVEEVDLSLRIFIQTLEANACREEYWLQTCSPFPLLFS

LCQLLDRFSKYWPLPKEKRCLSLDRKDLAIHILELLCEIVSANAETFSPD

VWIKSLSWLHRKLEQLDWTVGLRLKSFFEGHFKCEVPATLFEICKLSEDE

WTSQAHPGYGAGTGLLAWMECCCVSSGISERMLSLLVVDVGNPEEVRLFS

KGFLVALVQVMPWCSPQEWQRLHQLTRRLLEKQLLHVPYSLEYIQFVPLL

NLKPFAQELQLSVLFLRTFQFLCSHSCRNWLPLEGWNHVVKLLCGSLTRL

LDSVRAIQAAGPWVQGPEQDLTQEALFVYTQVFCHALHIMAMLHPEVCEP

LYVLALETLTCYETLSKTNPSVSSLLQRAHEQRFLKSIAEGIGPEERRQT

LLQKMSSF.
```

In another embodiment, the Gemin4 protein of the present invention comprises an amino acid sequence homologous to SEQ. ID. NO: 4. In another embodiment, the Gemin4 protein is a Homo sapiens Gemin4 protein. In another embodiment, the Gemin4 protein is from a non-human species. Each possibility represents a separate embodiment of the present invention.

In another embodiment, the Gemin protein is Gemin5 protein. In another embodiment, the sequence of the Gemin5 protein comprises the sequence:

```
                                         (SEQ. ID NO: 5)
MGQEPRTLPPSPNWYCARCSDAVPGGLFGFAARTSVFLVRVGPGAGESPG

TPPPFRVIGELVGHTERVSGFTFSHHPGQYNLCATSSDDGTVKIWDVETKT

VVTEHALHQHTISTLHWSPRVKDLIVSGDEKGVVFCYWFNRNDSQHLFIE

PRTIFCLTCSPHHEDLVAIGYKDGIVVIIDISKKGEVIHRLRGHDDEIHS

IAWCPLPGEDCLSINQEETSEEAEITNGNAVAQAPVTKGCYLATGSKDQT

IRIWSCSRGRGVMILKLPFLKRRGGGIDPTVKERLWLTLHWPSNQPTQLV

SSCFGGELLQWDLTQSWRRKYTLFSASSEGQNHSRIVFNLCPLQTEDDKQ

LLLSTSMDRDVKCWDIATLECSWTLPSLGGFAYSLAFSSVDIGSLAIGVG

DGMIRVWNTLSIKNNYDVKNFWQGVKSKVTALCWHPTKEGCLAFGTDDGK

VGLYDTYSNKPPQISSTYHKKTVYTLAWGPPVPPMSLGGEGDRPSLALYS

CGGEGIVLQHNPWKLSGEAFDINKLIRDTNSIKYKLPVHTEISWKADGKI

MALGNEDGSIEIFQIPNLKLICTIQQHHKLVNTISWHHEHGSQPELSYLM

ASGSNNAVIYVHNLKTVIESSPESPVTITEPYRTLSGHTAKITSVAWSPH

HDGRLVSASYDGTAQVWDALREEPLCNFRGHRGRLLCVAWSPLDPDCIYS

GADDFCVHKWLTSMQDHSRPPQGKKSIELEKKRLSQPKAKPKKKKKPTLR

TPVKLESIDGNEEESMKENSGPVENGVSDQEGEEQAREPELPCGLAPAVS

REPVICTPVSSGFEKSKVTINNKVILLKICEPPKEKPETLIKKRKARSLL

PLSTSLDHRSKEELHQDCLVLATAKHSRELNEDVSADVEERFHLGLFTDR

ATLYRMIDIEGKGHLENGHPELFHQLMLWKGDLKGVLQTAAERGELTDNL

VAMAPAAGYHVWLWAVEAFAKQLCFQDQYVKAASHLLSIHKVYEAVELLK

SNHFYREAIAIAKARLRPEDPVLKDLYLSWGTVLERDGHYAVAAKCYLGA
```

-continued

```
TCAYDAAKVLAKKGDAASLRTAAELAAIVGEDELSASLALRCAQELLLAN

NWVGAQEALQLHESLQGQRLVFCLLELLSRHLEEKQLSEGKSSSSYHTWN

TGTEGPFVERVTAVWKSIFSLDTPEQYQEAFQKLQNIKYPSATNNTPAKQ

LLLHICHDLTLAVLSQQMASWDEAVQALLRAVVRSYDSGSFTIMQEVYSA

FLPDGCDHLRDKLGDHQSPATPAFKSLEAFFLYGRLYEFWWSLSRPCPNS

SVWVRAGHRTLSVEPSQQLDTASTEETDPETSQPEPNRPSELDLRLTEEG

ERMLSTFKELFSEKHASLQNSQRTVAEVQETLAEM1RQHQKSQLCKSTAN

GPDKNEPEVEAEQPLCSSQSQCKEEKNEPLSLPELTKRLTEANQRMAKFP

ESIKAWPFPDVLECCLVLLLIRSHFPGCLAQEMQQQAQELLQKYGNTKTY

RRHCQTFCM.
```

In another embodiment, the Gemin5 protein of the present invention comprises an amino acid sequence homologous to SEQ. ID. NO: 5. In another embodiment, the Gemin5 protein is a Homo sapiens Gemin5 protein. In another embodiment, the Gemin5 protein is from a non-human species. Each possibility represents a separate embodiment of the present invention.

In another embodiment, the Gemin protein is Gemin6 protein. In another embodiment, the sequence of the Gemin6 protein comprises the sequence:

```
                                    (SEQ. ID NO: 6)
MSEWMKKGPLEWQDYIYKEVRVTASEKNEYKGWVLTTDPVSANIVLVNFL

EDGSMSVTGIMGHAVQTVETMNEGDHRVREKLMHLFTSGDCKAYSPEDLE

ERKNSLKKWLEKNHIPITEQGDAPRTLCVAGVLTIDPPYGPENCSSSNEI

ILSRVQDLIEGHLTASQ.
```

In another embodiment, the Gemin6 protein of the present invention comprises an amino acid sequence homologous to SEQ. ID. NO: 6. In another embodiment, the Gemin6 protein is a Homo sapiens Gemin6 protein. In another embodiment, the Gemin6 protein is from a non-human species. Each possibility represents a separate embodiment of the present invention.

In another embodiment, the Gemin protein is Gemin7 protein. In another embodiment, the sequence of the Gemin7 protein comprises the sequence:

```
                                    (SEQ. ID NO: 7)
MQTPVNIPVPVLRLPRGPDGFSRGFAPDGRRAPLRPEVPEIQECPIAQES

LESQEQRARAALRERYLRSLLAMVGHQVSFTLHEGVRVAAHFGATDLDVA

NFYVSQLQTPIGVQAEALLRCSDIISTYTFKP.
```

In another embodiment, the Gemin7 protein of the present invention comprises an amino acid sequence homologous to SEQ. ID. NO: 7. In another embodiment, the Gemin7 protein is a Homo sapiens Gemin7 protein. In another embodiment, the Gemin7 protein is from a non-human species. Each possibility represents a separate embodiment of the present invention.

In another embodiment, the Gemin protein of the present invention is a mouse Gemin. In another embodiment, the Gemin protein of the present invention is a rat Gemin. In another embodiment, the Gemin protein of the present invention is a Drosophila melanogaster Gemin. In another embodiment, the Gemin protein of the present invention is a baboon Gemin. In another embodiment, the Gemin protein of the present invention is a guinea pig Gemin. In another embodiment, the Gemin protein of the present invention is a Drosophila melanogaster Gemin. In another embodiment, the Gemin protein is from any other species known in the art. Each possibility represents a separate embodiment of the present invention.

In another embodiment, the Gemin protein of the present invention is at least 60% homologous to anyone SEQ. ID NOs: 1-7. In another embodiment, the Gemin protein of the present invention is at least 70% homologous to anyone SEQ. ID NOs: 1-7. In another embodiment, the Gemin protein of the present invention is at least 80% homologous to anyone SEQ. ID NOs: 1-7. In another embodiment, the Gemin protein of the present invention is at least 90% homologous to anyone SEQ. ID NOs: 1-7. In another embodiment, the Gemin protein of the present invention is at least 95% homologous to anyone SEQ. ID NOs: 1-7.

In another embodiment, protein synthesis according to the present invention comprises the multi-step process comprising the translation of the genetic information encoded in messenger RNAs (mRNAs) into proteins. In another embodiment, the method of the present invention is based on cellular localization of the survival of motor neurons protein (SMN). In another embodiment, protein synthesis inhibitors cause the SMN complex (and several of its Gemins) to relocalize from the cytoplasm to the nucleus. In another embodiment, protein synthesis inhibitors cause the SMN associated proteins to relocalize from the cytoplasm to the nucleus. In another embodiment, SMN associated proteins are Gemins.

In another embodiment, the SMN protein of the present invention oligomerizes and forms a stable multiprotein complex that comprises of SMN, Gemin2 (SIP1), Gemin3 (a DEAD-box RNA helicase), Gemin4, Gemin5 (a WD-repeat protein), Gemin6 and Gemin7. In another embodiment, SMN protein binds directly to Gemin 2, 3, 5 and 7, whereas Gemin 4 and 6 require Gemin3 and 7, respectively, for interaction with SMN. In another embodiment, other proteins bind to SMN protein. In another embodiment, these proteins, referred to as SMN complex substrates, include Sm and Sm-like (LSm) proteins, RNA helicase A, fibrillarin and GAR1, the RNP proteins hnRNP U, hnRNP Q and hnRNP R, as well as p80-coilin, the protein marker for Cajal (coiled) bodies.

In another embodiment, protein synthesis inhibitors cause the SMN protein and/or Gemins to relocalize from the cytoplasm to the nucleus within 1-48 hours. In another embodiment, protein synthesis inhibitors cause the SMN protein and/or Gemins to relocalize from the cytoplasm to the nucleus within 1-3 hours. In another embodiment, protein synthesis inhibitors cause the SMN protein and/or Gemins to relocalize from the cytoplasm to the nucleus within 3-5 hours. In another embodiment, protein synthesis inhibitors cause the SMN protein and/or Gemins to relocalize from the cytoplasm to the nucleus within 5-7 hours. In another embodiment, protein synthesis inhibitors cause the SMN protein and/or Gemins to relocalize from the cytoplasm to the nucleus within 7-9 hours. In another embodiment, protein synthesis inhibitors cause the SMN protein and/or Gemins to relocalize from the cytoplasm to the nucleus within 4-6 hours.

In another embodiment, protein synthesis inhibitors cause the SMN protein and/or Gemins to relocalize from the cytoplasm to the nucleus within 9-12 hours. In another embodiment, protein synthesis inhibitors cause the SMN protein and/or Gemins to relocalize from the cytoplasm to the nucleus within 12-15 hours. In another embodiment, protein synthesis inhibitors cause the SMN protein and/or Gemins to relocalize from the cytoplasm to the nucleus within 15-18 hours. In another embodiment, protein synthesis inhibitors cause the SMN protein and/or Gemins to relocalize from the cytoplasm to the nucleus within 18-21 hours. In another embodiment, protein synthesis inhibitors cause the SMN protein and/or Gemins to relocalize from the cytoplasm to the nucleus within 21-24 hours. In another embodiment, protein synthesis inhibitors cause the SMN protein and/or Gemins to relocalize from the cytoplasm to the nucleus within 24-30 hours. In another embodiment, protein synthesis inhibitors cause the SMN protein and/or Gemins to relocalize from the cytoplasm to the nucleus within 30-36 hours. In another embodiment, protein synthesis inhibitors cause the SMN protein and/or Gemins to relocalize from the cytoplasm to the nucleus within 36-42 hours. In another embodiment, protein synthesis inhibitors cause the SMN protein and/or Gemins to relocalize from the cytoplasm to the nucleus within 42-48 hours.

In another embodiment, protein synthesis inhibitors cause the SMN protein and/or Gemins to relocalize from the cytoplasm to the nucleus within 1-8 hours in HeLa cells. In another embodiment, protein synthesis inhibitors cause the SMN protein and/or Gemins to relocalize from the cytoplasm to the nucleus within 2-7 hours in HeLa cells. In another embodiment, protein synthesis inhibitors cause the SMN protein and/or Gemins to relocalize from the cytoplasm to the nucleus within 4-6 hours in HeLa cells.

In another embodiment, the candidate compound screened or tested according to the methods of the present invention is applied in a concentration of 0.1 $\mu$M-100 mM (example 3). In another embodiment, the candidate compound screened or tested according to the methods of the present invention is applied in a concentration of 0.1-4 $\mu$M. In another embodiment, the candidate compound screened or tested according to the methods of the present invention is applied in a concentration of 0.1-0.5 $\mu$M. In another embodiment, the candidate compound screened or tested according to the methods of the present invention is applied in a concentration of 1-2 $\mu$M. In another embodiment, the candidate compound screened or tested according to the methods of the present invention is applied in a concentration of 2-3 $\mu$M. In another embodiment, the candidate compound screened or tested according to the methods of the present invention is applied in a concentration of 3-5 $\mu$M. In another embodiment, the candidate compound screened or tested according to the methods of the present invention is applied in a concentration of 5-10 $\mu$M.

In another embodiment, the candidate compound screened or tested according to the methods of the present invention is applied in a concentration of 10-100 $\mu$M. In another embodiment, the candidate compound screened or tested according to the methods of the present invention is applied in a concentration of 100 $\mu$M-1 mM. In another embodiment, the candidate compound screened or tested according to the methods of the present invention is applied in a concentration of 1-5 mM. In another embodiment, the candidate compound screened or tested according to the methods of the present invention is applied in a concentration of 5-15 mM. In another embodiment, the candidate compound screened or tested according to the methods of the present invention is applied in a concentration of 15-30 mM. In another embodiment, the candidate compound screened or tested according to the methods of the present invention is applied in a concentration of 30-50 mM. In another embodiment, the candidate compound screened or tested according to the methods of the present invention is applied in a concentration of 50-75 mM. In another embodiment, the candidate compound screened or tested according to the methods of the present invention is applied in a concentration of 75-100 mM.

In another embodiment, the method of the present invention is carried out using cells cultured in miniaturized format. In another embodiment, cells cultured in miniaturized format of the present invention comprise multi-well plates. In another embodiment, a multi-well plate of the present invention comprises 96 wells. In another embodiment, a multi-well plate of the present invention comprises 384 wells (example 2). In another embodiment, a multi-well plate of the present invention comprises 1536 wells. In another embodiment, a multi-well plate of the present invention comprises from 2-5000 wells. In another embodiment, a multi-well plate of the present invention comprises from 20-3000 wells. In another embodiment, a multi-well plate of the present invention comprises from 96-2000 wells.

In another embodiment, the cells of the present invention are treated for several hours as indicated hereinabove in the presence of compounds that potentially inhibit protein synthesis (example 3). In another embodiment, the cells of the present invention are treated in the presence of small molecules that potentially inhibit protein synthesis. In another embodiment, the cells of the present invention are then fixed. In another embodiment, the cells of the present invention are further permeabilized. In another embodiment, the cells of the present invention are further contacted with an SMN specific ligand. In another embodiment, the SMN specific ligand labels the SMC complex components. In another embodiment, the SMN specific ligand labels SMC complex component.

In another embodiment, the labeled SMN complex component is then detected. In another embodiment, the labeled SMN complex component is then detected by microscopy. In another embodiment, digital images record the microscopic images. In another embodiment, the digital images are collected from several fields in each well. In another embodiment, the microscopic images collected from several fields in each well are further analyzed by algorithmic imaging software. In another embodiment, the algorithmic imaging software monitors the amount of labeled an SMN complex component in the nucleus. In another embodiment, the algorithmic imaging software monitors the relative amount of labeled an SMN complex component in the nucleus. In another embodiment, the nucleus is defined by the signal of a nuclear specific stain. In another embodiment, the cytoplasm is defined by the signal of a cytoplasmic specific stain. In another embodiment, the nucleus signal is collected in a separate channel from the labeled an SMN complex component (example 2).

In another embodiment, the present invention provides method identifying inhibitors of protein translation. In another embodiment, a method for identifying inhibitors of protein translation can avoid dysregulated, protein synthesis in disease. In another embodiment, a method for identifying inhibitors of protein translation can avoid enhanced protein synthesis in disease. In another embodiment, the ribosome recruitment phase of translation initiation is usurped in many human cancers. In another embodiment, the protein synthesis inhibitors identified by the methods of the present invention block signaling events promoting cancer.

In another embodiment, the present invention provides method for identifying inhibitors of protein elongation. In another embodiment, inhibitors of protein elongation have direct consequence of protein synthesis inhibition. In another embodiment, inhibitors of protein elongation identified by the methods of the present invention are anti-cancer agents. In another embodiment, inhibitors of protein synthesis of the present invention target ABL protein. In another embodiment, inhibitors of protein synthesis of the present invention target PDGFR protein. In another embodiment, inhibitors of protein synthesis of the present invention target KIT protein.

In another embodiment, inhibitors of protein synthesis identified by the methods of the present invention can treat breast cancer. In another embodiment, inhibitors of protein synthesis identified by the methods of the present invention can treat prostate cancer. In another embodiment, inhibitors of protein synthesis identified by the methods of the present invention can leukemia. In another embodiment, inhibitors of protein synthesis identified by the methods of the present invention can treat chronic myeloid leukemia. In another embodiment, inhibitors of protein synthesis identified by the methods of the present invention can treat skin cancer. In another embodiment, inhibitors of protein synthesis identified by the methods of the present invention can treat colorectal cancer. In another embodiment, inhibitors of protein synthesis identified by the methods of the present invention can treat premalignant polyps. In another embodiment, inhibitors of protein synthesis identified by the methods of the present invention can treat mammary adenocarcinoma. In another embodiment, inhibitors of protein synthesis identified by the methods of the present invention can treat mantle cell lymphoma. In another embodiment, inhibitors of protein synthesis identified by the methods of the present invention can treat oral squamous cell carcinoma. In another embodiment, inhibitors of protein synthesis identified by the methods of the present invention can treat pancreatic tumors. In another embodiment, inhibitors of protein synthesis identified by the methods of the present invention can treat bladder cancer. In another embodiment, inhibitors of protein synthesis identified by the methods of the present invention can treat lung cancer. In another embodiment, inhibitors of protein synthesis identified by the methods of the present invention can treat gastrointestinal tumors. In another embodiment, inhibitors of protein synthesis identified by the methods of the present invention can treat head tumors. In another embodiment, inhibitors of protein synthesis identified by the methods of the present invention can treat neck tumors. In another embodiment, inhibitors of protein synthesis identified by the methods of the present invention can treat Hodgkin's lymphoma. In another embodiment, inhibitors of protein synthesis identified by the methods of the present invention can treat neuroblastoma.

In another embodiment, inhibitors of protein synthesis of the present invention are screened or tested on a primary cell culture derived from a tumor. In another embodiment, inhibitors of protein synthesis of the present invention are screened or tested on a primary cell culture derived from a cancer patient suffering from one of the cancers listed hereinabove. In another embodiment, inhibitors of protein synthesis of the present invention are screened or tested on a cancer cell line. In another embodiment, inhibitors of protein synthesis of the present invention are screened or tested on a cancer cell line of a hematopoietic lineage.

In another embodiment, the methods of the present invention are preformed on a cell.

In another embodiment, the cell of the present invention is a eukaryotic cell. In another embodiment, the cell of the present invention is an epidermal keratinocyte. In another embodiment, the cell of the present invention is an epidermal basal cell. In another embodiment, the cell of the present invention is a keratinocyte of fingernails or toenails. In another embodiment, the cell of the present invention is a nail bed basal cell. In another embodiment, the cell of the present invention is a stem cell. In another embodiment, the cell of the present invention is a medullary hair shaft cell. In another embodiment, the cell of the present invention is a cortical hair shaft cell. In another embodiment, the cell of the present invention is a cuticular hair shaft cell. In another embodiment, the cell of the present invention is a cuticular hair root sheath cell. In another embodiment, the cell of the present invention is a hair root sheath cell of Huxley's layer. In another embodiment, the cell of the present invention is a hair root sheath cell of Henle's layer. In another embodiment, the cell of the present invention is an external hair root sheath cell. In another embodiment, the cell of the present invention is a hair matrix cell. In another embodiment, the cell of the present invention is a prokaryotic cell.

In another embodiment, the cell of the present invention is a wet stratified barrier epithelial cell. In another embodiment, the cell of the present invention is a surface epithelial cell of stratified squamous epithelium of the cornea. In another embodiment, the cell of the present invention is a surface epithelial cell of stratified squamous epithelium of the tongue. In another embodiment, the cell of the present invention is a surface epithelial cell of stratified squamous epithelium of the oral cavity. In another embodiment, the cell of the present invention is a surface epithelial cell of stratified squamous epithelium of the esophagus. In another embodiment, the cell of the present invention is a surface epithelial cell of stratified squamous epithelium of the anal canal. In another embodiment, the cell of the present invention is a surface epithelial cell of stratified squamous epithelium of the distal urethra. In another embodiment, the cell of the present invention is a surface epithelial cell of stratified squamous epithelium of the vagina.

In another embodiment, the cell of the present invention is a basal cell of epithelia of the cornea. In another embodiment, the cell of the present invention is a basal cell of epithelia of the tongue. In another embodiment, the cell of the present invention is a basal cell of epithelia of the oral cavity. In another embodiment, the cell of the present invention is a basal cell of epithelia of the esophagus. In another embodiment, the cell of the present invention is a basal cell of epithelia of the anal canal. In another embodiment, the cell of the present invention is a basal cell of epithelia of the distal urethra. In another embodiment, the cell of the present invention is a basal cell of epithelia of the vagina.

In another embodiment, the cell of the present invention is a urinary epithelium cell. In another embodiment, the cell of the present invention is an exocrine secretory epithelial cell. In another embodiment, the cell of the present invention is a salivary gland mucous cell. In another embodiment, the cell of the present invention is a salivary gland serous cell. In another embodiment, the cell of the present invention is a Von Ebner's gland cell. In another embodiment, the cell of the present invention is a mammary gland cell. In another embodiment, the cell of the present invention is a lacrimal gland cell. In another embodiment, the cell of the present invention is a ceruminous gland cell. In another embodiment, the cell of the present invention is an eccrine sweat gland dark cell. In another embodiment, the cell of the present invention is an eccrine sweat gland clear cell. In another embodiment, the cell of the present invention is an apocrine sweat gland cell. In another embodiment, the cell of the present invention is a gland of moll cell. In another embodiment, the cell of the present invention is a sebaceous gland cell. In another embodiment, the cell of the present invention is a Bowman's gland cell. In another embodiment, the cell of the present invention is a Brunner's gland cell. In another embodiment, the cell of the present invention is a seminal vesicle cell. In another embodiment, the cell of the present invention is a prostate gland cell. In another embodiment, the cell of the present invention is a bulbourethral gland cell. In another embodiment, the cell of the present invention is a Bartholin's gland cell. In another embodiment, the cell of the present invention is a gland of Littre cell. In another embodiment, the cell of the present invention is a uterus endometrium cell. In another embodiment, the cell of the present invention is a goblet cell. In another embodiment, the cell of the present invention is a stomach lining mucous cell.

In another embodiment, the cell of the present invention is a gastric gland cell. In another embodiment, the cell of the present invention is a gastric gland zymogenic cell. In another embodiment, the cell of the present invention is a gastric gland oxyntic cell. In another embodiment, the cell of the present invention is a pancreatic cell. In another embodiment, the cell of the present invention is a pancreatic acinar cell. In another embodiment, the cell of the present invention is a paneth cell. In another embodiment, the cell of the present invention is a pneumocyte. In another embodiment, the cell of the present invention is a Clara cell of lung.

In another embodiment, the cell of the present invention is a hormone secreting cell. In another embodiment, the cell of the present invention is an anterior pituitary cell. In another embodiment, the cell of the present invention is a somatotrope. In another embodiment, the cell of the present invention is a lactotrope. In another embodiment, the cell of the present invention is a thyrotrope. In another embodiment, the cell of the present invention is a gonadotrope. In another embodiment, the cell of the present invention is a corticotrope. In another embodiment, the cell of the present invention is an intermediate pituitary cell. In another embodiment, the cell of the present invention is a magnocellular neurosecretory cell. In another embodiment, the cell of the present invention is an oxytocin secreting cell. In another embodiment, the cell of the present invention is a serotonin secreting cell. In another embodiment, the cell of the present invention is an endorphin secreting cell. In another embodiment, the cell of the present invention is a somatostatin secreting cell. In another embodiment, the cell of the present invention is a gastrin secreting cell. In another embodiment, the cell of the present invention is a secretin secreting cell. In another embodiment, the cell of the present invention is a cholecystokinin secreting cell. In another embodiment, the cell of the present invention is an insulin secreting cell. In another embodiment, the cell of the present invention is a glucagon secreting cell. In another embodiment, the cell of the present invention is a bombesin secreting cell. In another embodiment, the cell of the present invention is a thyroid gland cell. In another embodiment, the cell of the present invention is a thyroid epithelial cell. In another embodiment, the cell of the present invention is a parafollicular cell. In another embodiment, the cell of the present invention is a parathyroid gland cell. In another embodiment, the cell of the present invention is a parathyroid chief cell. In another embodiment, the cell of the present invention is an oxyphil cell.

In another embodiment, the cell of the present invention is an adrenal gland cell. In another embodiment, the cell of the present invention is a chromaffin cell. In another embodiment, the cell of the present invention is a steroid hormones secreting cell. In another embodiment, the cell of the present invention is a Leydig cell. In another embodiment, the cell of the present invention is a theca interna cell. In another embodiment, the cell of the present invention is a corpus luteum cell. In another embodiment, the cell of the present invention is a kidney juxtaglomerular apparatus cell. In another embodiment, the cell of the present invention is a macula densa cell. In another embodiment, the cell of the present invention is a peripolar cell. In another embodiment, the cell of the present invention is a mesangial cell. In another embodiment, the cell of the present invention is an intestinal brush border cell. In another embodiment, the cell of the present invention is an exocrine gland striated duct cell. In another embodiment, the cell of the present invention is a gall bladder epithelial cell. In another embodiment, the cell of the present invention is a kidney proximal tubule brush border cell. In another embodiment, the cell of the present invention is a kidney distal tubule cell. In another embodiment, the cell of the present invention is a ductulus efferens nonciliated cell. In another embodiment, the cell of the present invention is an epididymal principal cell. In another embodiment, the cell of the present invention is an epididymal basal cell.

In another embodiment, the cell of the present invention is a storage cell. In another embodiment, the cell of the present invention is a hepatocyte. In another embodiment, the cell of the present invention is a white fat cell. In another embodiment, the cell of the present invention is a brown fat cell. In another embodiment, the cell of the present invention is a liver lipocyte.

In another embodiment, the cell of the present invention is a barrier function cell. In another embodiment, the cell of the present invention is a type I pneumocyte. In another embodiment, the cell of the present invention is a pancreatic duct cell. In another embodiment, the cell of the present invention is a nonstriated duct cell. In another embodiment, the cell of the present invention is a kidney glomerulus parietal cell. In another embodiment, the cell of the present invention is a kidney glomerulus podocyte. In another embodiment, the cell of the present invention is a loop of Henle thin segment cell. In another embodiment, the cell of the present invention is a kidney collecting duct cell. In another embodiment, the cell of the present invention is a duct cell. In another embodiment, the cell of the present invention is an epithelial cell lining closed internal body cavity. In another embodiment, the cell of the present invention is a blood vessel cell. In another embodiment, the cell of the present invention is a lymphatic vascular endothelial fenestrated cell. In another embodiment, the cell of the present invention is a blood vessel or lymphatic vascular endothelial continuous cell. In another embodiment, the cell of the present invention is a blood vessel or lymphatic vascular endothelial splenic cell. In another embodiment, the cell of the present invention is a synovial cell. In another embodiment, the cell of the present invention is a serosal cell. In another embodiment, the cell of the present invention is a squamous cell. In another embodiment, the cell of the present invention is a columnar cell of endolymphatic sac with microvilli. In another embodiment, the cell of the present invention is a columnar cell of endolymphatic sac without microvilli. In another embodiment, the cell of the present invention is a dark cell. In another embodiment, the cell of the present invention is a vestibular membrane cell. In another embodiment, the cell of the present invention is a stria vascularis basal cell. In another embodiment, the cell of the present invention is a stria vascularis marginal cell. In another embodiment, the cell of the present invention is a cell of Claudius. In another embodiment, the cell of the present invention is a cell of Boettcher. In another embodiment, the cell of the present invention is a choroid plexus cell. In another embodiment, the cell of the present invention is a pia-arachnoid squamous cell. In another embodiment, the cell of the present invention is a pigmented ciliary epithelium cell. In another embodiment, the cell of the present invention is a nonpigmented ciliary epithelium cell. In another embodiment, the cell of the present invention is a corneal endothelial cell. In another embodiment, the cell of the present invention is a ciliated cell with propulsive function. In another embodiment, the cell of the present invention is a respiratory tract ciliated cell. In another embodiment, the cell of the present invention is an oviduct ciliated cell. In another embodiment, the cell of the present invention is a uterine endometrial ciliated cell. In another embodiment, the cell of the present invention is a rete testis cilated cell. In another embodiment, the cell of the present invention is a ductulus efferens ciliated cell. In another embodiment, the cell of the present invention is a ciliated ependymal cell of central nervous system.

In another embodiment, the cell of the present invention is an extracellular matrix secretion cell. In another embodiment, the cell of the present invention is an ameloblast epithelial cell. In another embodiment, the cell of the present invention is a planum semilunatum epithelial cell. In another embodiment, the cell of the present invention is an organ of Corti interdental epithelial cell. In another embodiment, the cell of the present invention is a fibroblast. In another embodiment, the cell of the present invention is a loose connective tissue fibroblast. In another embodiment, the cell of the present invention is a corneal fibroblast. In another embodiment, the cell of the present invention is a tendon fibroblast. In another embodiment, the cell of the present invention is a bone marrow reticular tissue fibroblast. In another embodiment, the cell of the present invention is a nonepithelial fibroblast. In another embodiment, the cell of the present invention is a pericyte. In another embodiment, the cell of the present invention is a nucleus pulposus cell of intervertebral disc. In another embodiment, the cell of the present invention is a cementoblast. In another embodiment, the cell of the present invention is a cementocyte. In another embodiment, the cell of the present invention is an odontoblast. In another embodiment, the cell of the present invention is an odontocyte.

In another embodiment, the cell of the present invention is a chondrocyte. In another embodiment, the cell of the present invention is a hyaline cartilage chondrocyte. In another embodiment, the cell of the present invention is a fibrocartilage chondrocyte. In another embodiment, the cell of the present invention is an elastic cartilage chondrocyte. In another embodiment, the cell of the present invention is an osteoblast. In another embodiment, the cell of the present invention is an osteocyte. In another embodiment, the cell of the present invention is an osteoprogenitor cell. In another embodiment, the cell of the present invention is a hyalocyte. In another embodiment, the cell of the present invention is a stellate cell. In another embodiment, the cell of the present invention is a contractile cell.

In another embodiment, the cell of the present invention is a muscle cell. In another embodiment, the cell of the present invention is a red skeletal muscle cell. In another embodiment, the cell of the present invention is a white skeletal muscle cell. In another embodiment, the cell of the present invention is an intermediate skeletal muscle cell. In another embodiment, the cell of the present invention is a nuclear bag cell. In another embodiment, the cell of the present invention is a nuclear chain cell. In another embodiment, the cell of the present invention is a satellite cell. In another embodiment, the cell of the present invention is a heart muscle cell. In another embodiment, the cell of the present invention is a nodal heart muscle cell. In another embodiment, the cell of the present invention is a purkinje fiber cell. In another embodiment, the cell of the present invention is a smooth muscle cell. In another embodiment, the cell of the present invention is a myoepithelial cell.

In another embodiment, the cell of the present invention is a blood cell. In another embodiment, the cell of the present invention is an immune system cell. In another embodiment, the cell of the present invention is a red blood cell. In another embodiment, the cell of the present invention is a megakaryocyte. In another embodiment, the cell of the present invention is a monocyte. In another embodiment, the cell of the present invention is macrophage. In another embodiment, the cell of the present invention is an epidermal Langerhans cell. In another embodiment, the cell of the present invention is an osteoclast. In another embodiment, the cell of the present invention is a dendritic cell. In another embodiment, the cell of the present invention is a microglial cell. In another embodiment, the cell of the present invention is a neutrophil. In another embodiment, the cell of the present invention is an eosinophil. In another embodiment, the cell of the present invention is a basophile. In another embodiment, the cell of the present invention is a mast cell.

In another embodiment, the cell of the present invention is a T-Helper cell. In another embodiment, the cell of the present invention is a T-suppressor cell. In another embodiment, the cell of the present invention is a cytotoxic T cell. In another embodiment, the cell of the present invention is a B cell. In another embodiment, the cell of the present invention is a natural killer cell. In another embodiment, the cell of the present invention is a reticulocyte. In another embodiment, the cell of the present invention is a stem cell. In another embodiment, the cell of the present invention is a committed progenitor for the blood and immune system.

In another embodiment, the cell of the present invention is a sensory transducer cell. In another embodiment, the cell of the present invention is an auditory inner hair cell of organ of Corti. In another embodiment, the cell of the present invention is an auditory outer hair cell of organ of Corti. In another embodiment, the cell of the present invention is a basal olfactory epithelium cell. In another embodiment, the cell of the present invention is a cold-sensitive primary sensory neuron. In another embodiment, the cell of the present invention is a heat-sensitive primary sensory neuron. In another embodiment, the cell of the present invention is a merkel cell. In another embodiment, the cell of the present invention is an olfactory receptor neuron. In another embodiment, the cell of the present invention is a pain-sensitive primary sensory neuron. In another embodiment, the cell of the present invention is a photoreceptor rod cell. In another embodiment, the cell of the present invention is a photoreceptor blue-sensitive cone cell. In another embodiment, the cell of the present invention is a photoreceptor green-sensitive cone cell. In another embodiment, the cell of the present invention is a photoreceptor red-sensitive cone cell. In another embodiment, the cell of the present invention is a proprioceptive primary sensory neuron. In another embodiment, the cell of the present invention is a touch-sensitive primary sensory neuron. In another embodiment, the cell of the present invention is a type I carotid body cell. In another embodiment, the cell of the present invention is a type II carotid body cell. In another embodiment, the cell of the present invention is a type I hair cell of vestibular apparatus. In another embodiment, the cell of the present invention is a type II hair cell of vestibular apparatus. In another embodiment, the cell of the present invention is a type I taste bud cell. In another embodiment, the cell of the present invention is an autonomic neuron cell. In another embodiment, the cell of the present invention is a cholinergic neural cell. In another embodiment, the cell of the present invention is an adrenergic neural cell. In another embodiment, the cell of the present invention is a peptidergic neural cell. In another embodiment, the cell of the present invention is a sense organ or peripheral neuron supporting cell. In another embodiment, the cell of the present invention is an inner pillar cell of organ of Corti. In another embodiment, the cell of the present invention is an outer pillar cell of organ of Corti. In another embodiment, the cell of the present invention is an inner phalangeal cell of organ of Corti. In another embodiment, the cell of the present invention is an outer phalangeal cell of organ of Corti. In another embodiment, the cell of the present invention is a border cell of organ of Corti. In another embodiment, the cell of the present invention is a Hensen cell of organ of Corti. In another embodiment, the cell of the present invention is a vestibular apparatus supporting cell. In another embodiment, the cell of the present invention is a type I taste bud supporting cell. In another embodiment, the cell of the present invention is an olfactory epithelium supporting cell. In another embodiment, the cell of the present invention is a Schwann cell. In another embodiment, the cell of the present invention is a satellite cell encapsulating peripheral nerve cell bodies. In another embodiment, the cell of the present invention is an enteric glial cell.

In another embodiment, the cell of the present invention is a central nervous system neuron. In another embodiment, the cell of the present invention is a glial cell. In another embodiment, the cell of the present invention is an astrocyte. In another embodiment, the cell of the present invention is an oligodendrocyte. In another embodiment, the cell of the present invention is a spindle neuron. In another embodiment, the cell of the present invention is a lens cell. In another embodiment, the cell of the present invention is an anterior lens epithelial cell. In another embodiment, the cell of the present invention is a crystalline-containing lens fiber cell. In another embodiment, the cell of the present invention is a karan cell. In another embodiment, the cell of the present invention is a pigment cell. In another embodiment, the cell of the present invention is a melanocyte. In another embodiment, the cell of the present invention is a retinal pigmented epithelial cell.

In another embodiment, the cell of the present invention is a germ cell. In another embodiment, the cell of the present invention is an oogonium. In another embodiment, the cell of the present invention is an oocyte. In another embodiment, the cell of the present invention is a spermatid. In another embodiment, the cell of the present invention is a spermatocyte. In another embodiment, the cell of the present invention is a spermatogonium cell. In another embodiment, the cell of the present invention is a spermatozoon.

In another embodiment, the cell of the present invention is a nurse cell. In another embodiment, the cell of the present invention is an ovarian follicle cell. In another embodiment, the cell of the present invention is a sertoli cell. In another embodiment, the cell of the present invention is a thymus epithelial cell.

In another embodiment, the cell of the present invention is derived from an organ. In another embodiment, the cell of the present invention is derived from a tissue. In another embodiment, the cell of the present invention is derived from a cell line. In another embodiment, the cell of the present invention is derived from a primary cell culture. In another embodiment, the cell of the present invention is a HeLa cell. In another embodiment, the cell of the present invention is a U2OS cell.

In another embodiment, the cell of the present invention is a plant cell. In another embodiment, the cell of the present invention is an invertebrate cell. In another embodiment, the cell of the present invention is a vertebrate cell. In another embodiment, the cell of the present invention is an insect cell. In another embodiment, the cell of the present invention is an amphibian cell. In another embodiment, the cell of the present invention is a reptile cell. In another embodiment, the cell of the present invention is a mammalian cell.

In another embodiment, the present invention provides a tissue section in which individual cells are analyzed.

In one embodiment, the present invention provides a method for the selective capture of a SMN complex component with a ligand. In another embodiment, the ligand of the invention binds Gem. In another embodiment, the ligand of the invention selectively binds Gem. In another embodiment, the ligand of the invention binds a Gemin protein. In another embodiment, the ligand of the invention selectively binds a Gemin protein.

In another embodiment, the ligand of the present invention is an antibody.

In another embodiment, the ligand is a polyclonal antibody. In another embodiment, the ligand is a monoclonal antibody. In another embodiment, the monoclonal antibody is a monovalent Fab fragments. In another embodiment, the monoclonal antibody is a Bivalent mini-antibodies (equivalent to F(ab')2 fragments). In another embodiment, the monoclonal antibody is comprised of a genetic fusion to a variety of common protein tags.

In another embodiment, the antibody of the present invention is a multiple engineered specificity antibody. In another embodiment, bispecific antibodies contain two different binding specificities fused together. In another embodiment, bispecific antibodies of the invention bind to two adjacent epitopes on a single target antigen. In another embodiment, bispecific antibodies of the invention bind to two adjacent epitopes on the SMN complex. In another embodiment, bispecific antibodies of the invention cross-link two different antigens. In another embodiment, Bispecific antibodies of the present invention are produced by fusion of two hybridoma cell lines into a single 'quadroma' cell line. In another embodiment, effective methods to couple two different Fab modules of the invention incorporate either chemical conjugation. In another embodiment, effective methods to couple two different Fab modules of the invention incorporate either genetic conjugation. In another embodiment, effective methods to couple two different Fab modules of the invention incorporate fusion to adhesive heterodimeric domains.

In another embodiment, the antibody of the present invention is a bifunctional antibodie. In another embodiment, the antibody of the present invention is fused to radio labeled moiety. In another embodiment, the antibody of the present invention is fused to an enzyme.

In another embodiment, the antibody of the present invention is derived from antibody libraries. In another embodiment, the antibody of the present invention is a specific high-affinity antibody selected by linking phenotype (binding affinity) to genotype, thereby allowing simultaneous recovery of the gene encoding the selected antibody.

In another embodiment, the antibody of the present invention is comprised of single-chain Fv fragments. In another embodiment, the single-chain Fv fragments antibody of the present invention contain a complete binding site and consist of the individual heavy and light chain V domain (12-14 kDa each). In another embodiment, the single-chain Fv fragments antibody of the present invention is linked to a single protein by a hydrophilic and flexible polypeptide linker. In another embodiment, the single-chain Fv fragments antibody of the present invention additionally include also a His tag. In another embodiment, the single-chain Fv fragments antibody of the present invention additionally includes an immuno-detection epitope. In another embodiment, the single-chain Fv fragments antibody of the present invention additionally includes a protease specific cleavage site. In another embodiment, the linker of the variable region domains (carboxyl ter-minus of the VL sequence to the amino terminus of the VH sequence) has to be long enough to span the distance from the C-terminus of one domain to the N-terminus of the second domain (about 3.5 nm).

In another embodiment, the antibody according to the methods of the present invention binds a protein within the SMN complex. In another embodiment, the antibody according to the methods of the present invention is a monoclonal anti-SMN protein antibody. In another embodiment, the antibody according to the methods of the present invention is the anti-SMN monoclonal antibody 2B1. In another embodiment, the 2B1 antibody of the present invention binds Gems. In another, embodiment, 2B1 antibody binds cytoplasmic Gems. In another, embodiment, 2B1 antibody binds nuclear Gems (See example 1). In another embodiment, the antibody of the present invention binds Gemin1. In another embodiment, the antibody of the present invention binds Gemin2. In another embodiment, the antibody of the present invention binds Gemin3. In another embodiment, the antibody of the present invention binds Gemin4. In another embodiment, the antibody of the present invention binds Gemin5. In another embodiment, the antibody of the present invention binds Gemin6. In another embodiment, the antibody of the present invention binds Gemin7 (example 5, FIG. 4).

In another embodiment, the ligand of the present invention is labeled.

In another embodiment, the antibody of the present invention is labeled. In another embodiment, the labeled antibody of the present invention is a fluorescent labeled antibody. In another embodiment, the label is Alexa Fluor. In another embodiment, the label is green fluorescent protein. In another embodiment, the label is Oregon green. In another embodiment, the label is Emerald. In another embodiment, the label is Azami Green. In another embodiment, the label is ZsGreen 1. In another embodiment, the label is a blue fluorescent protein. In another embodiment, the label is EBFP. In another embodiment, the label is Sapphire. In another embodiment, the label is a cyan fluorescent protein. In another embodiment, the label is cerulean. In another embodiment, the label is ECFP. In another embodiment, the label is AmCyan. In another embodiment, the label is Midoriishi-Cyan. In another embodiment, the label is a yellow fluorescent protein. In another embodiment, the label is ZsYellow1. In another embodiment, the label is PhiYFP. In another embodiment, the label is Citrine. In another embodiment, the label is Venus. In another embodiment, the label is an orange fluorescent protein. In another embodiment, the label is Kusabira-Orange. In another embodiment, the label is mOrange. In another embodiment, the label is a red fluorescent protein. In another embodiment, the label is DsRed. In another embodiment, the label is HcRed. In another embodiment, the label is mPlum. In another embodiment, the label is mRaspberry. In another embodiment, the label is mTomato. In another embodiment, the label is mStrawberry. In another embodiment, the label is green-to-red fluorescent Dendra.

In another embodiment, the present invention provides a SMN complex component is fused to a fluorescent probe.

In another embodiment, an identifiable gene product serves as a distinguishable marker for a SMN complex component. In another embodiment, the methods of the present invention provide a Gemin protein fused to a fluorescent probe of the invention. In another embodiment, the methods of the present invention provide that a SMN complex component is a chimera comprising a SMN complex component and a fluorescent protein.

In another embodiment, the label of the present invention is a radioactive label. In another embodiment, a ligand of the present invention is radioactively labeled with $^{32}$P. In another embodiment, an antibody of the present invention is radioactively labeled with $^{32}$P. In another embodiment, a ligand of the present invention is radioactively labeled with $^{125}$I. In another embodiment, an antibody of the present invention is radioactively labeled with $^{125}$I. In another embodiment, the label of the present invention is a chemiluminescent label. In another embodiment, the label of the present invention is a gold label.

In some embodiments, the detection method is indirect comprising a ligand of the present invention similar to immunohistochemical probes as known to one skilled in the art. In another embodiment, probes may be labeled with hapten or biotin used to bring an enzyme which creates a detectable event (e.g., chemiluminescent, colorimetric or fluorescent) to the SMN complex component site. In another embodiment, wherein amplification of the detection signal is required, a secondary labeled antibody specifically identifying the primary antibody is utilized. In another embodiment, the methods utilizing a specific probe comprising an antibody enable selective identification of an SMN component.

In another embodiment, the method of the present invention provides measuring the level of an SMN complex component relocalization from the cytoplasm to the nucleus. In another embodiment, the method of the present invention provides measuring an SMN complex component in the nucleus and cytoplasm of said cell. In another embodiment, the method of the present invention provides an absolute number of an SMN complex component in the nucleus and cytoplasm.

In another embodiment, the present invention provides a method of testing a candidate compound for an ability to inhibit protein synthesis, comprising the steps of contacting a cell with a candidate compound; and measuring the level of a SMN complex component in the cytoplasm of a cell, the nucleus of a cell, or a combination thereof, whereby, if a candidate compound increases the amount of the SMN complex component in the nucleus, decreases the amount of the SMN complex component in the cytoplasm, or a combination thereof, then the compound exhibits an ability to inhibit protein synthesis.

In another embodiment, the present invention further provides detection of pro-apoptotic cell derived compounds (e.g. hormones, growth factors, nitric oxide, or cytokines) that are measured according to methods known to one of skill in the art. In another embodiment, inhibition of protein synthesis is measured according to the methods of the present invention in cells secreting pro-apoptotic compounds. In another embodiment, induction of protein synthesis is measured according to the methods of the present invention in cells secreting pro-apoptotic compounds. In another embodiment, inhibition of protein synthesis is measured according to the methods of the present invention in cells undergoing apoptosis. In another embodiment, induction of protein synthesis is measured according to the methods of the present invention in cells undergoing apoptosis.

In another embodiment, ability to decrease protein synthesis correlates with ability to induce the expression of pro-apoptotic cytokines or hormones in a target cell. In another embodiment, ability to decrease protein synthesis correlates with ability to induce the pro-apoptotic oxidative stress in a target cell. In another embodiment, ability to inhibit protein synthesis correlates with ability to induce the expression of pro-apoptotic cytokines or hormones in a target cell. In another embodiment, ability to induce protein synthesis correlates with ability to induce the expression of pro-apoptotic cytokines or hormones in a target cell. In another embodiment, ability to increase protein synthesis correlates with ability to induce the expression of pro-apoptotic cytokines or hormones in a target cell. In another embodiment, ability to increase protein synthesis correlates with ability to induce pro-apoptotic oxidative stress in a target cell. In another embodiment, ability to increase protein synthesis correlates with ability to induce pro-apoptotic nitric oxide (NO) stress in a target cell.

In another embodiment, induction of apoptosis by a candidate compound of the present invention correlates with a steady state level of protein synthesis. In another embodiment, induction of expression of pro-apoptotic cytokines in a target cell by a candidate compound of the present invention correlates with a steady state level of protein synthesis. In another embodiment, inhibition of apoptosis by a candidate compound of the present invention correlates with a steady state level of protein synthesis. In another embodiment, inhibition of expression of pro-apoptotic cytokines or hormones in a target cell by a candidate compound of the present invention correlates with a steady state level of protein synthesis. In another embodiment, inhibition of pro-apoptotic NO in a target cell by a candidate compound of the present invention correlates with a steady state level of protein synthesis.

In another embodiment, the present invention provides a method of testing a candidate compound for an ability to inhibit protein synthesis dependent necrosis, comprising the steps of contacting a cell with a candidate compound; and measuring the level of a SMN complex component in the cytoplasm of a cell, the nucleus of a cell, or a combination thereof, whereby, if a candidate compound increases the amount of the SMN complex component in the nucleus, decreases the amount of the SMN complex component in the cytoplasm, or a combination thereof, then the compound exhibits an ability to inhibit protein synthesis.

In another embodiment, the present invention further provides detection of pro-necrotic cell derived compounds (e.g. hormones, growth factors, nitric oxide, or cytokines) that are measured according to methods known to one of skill in the art. In another embodiment, protein synthesis inhibition or induction is measured according to the methods of the present invention in cells undergoing necrosis. In another embodiment, induction protein synthesis is measured according to the methods of the present invention in cells undergoing necrosis.

In another embodiment, ability to decrease protein synthesis correlates with ability to induce stress in a target cell. In another embodiment, ability to decrease protein synthesis correlates with ability to induce oxidative stress in a target cell. In another embodiment, ability to decrease protein synthesis correlates with ability to induce hypoxia in a target cell. In another embodiment, ability to decrease protein synthesis correlates with starving a target cell. In another embodiment, ability to decrease protein synthesis correlates with ability to induce necrosis in a target cell. In another embodiment, ability to inhibit protein synthesis correlates with ability to induce necrosis in a target cell.

In another embodiment, ability to increase protein synthesis correlates with ability to induce stress in a target cell. In another embodiment, ability to increase protein synthesis correlates with ability to induce oxidative stress in a target cell. In another embodiment, ability to increase protein synthesis correlates with ability to induce hypoxia in a target cell. In another embodiment, ability to increase protein synthesis correlates with starving a target cell. In another embodiment, ability to increase protein synthesis correlates with ability to induce necrosis in a target cell.

In another embodiment, induction of necrosis by a candidate compound of the present invention correlates with a steady state level of protein synthesis. In another embodiment, induction of expression of pro-necrotic cytokines in a target cell by a candidate compound of the present invention correlates with a steady state level of protein synthesis. In another embodiment, inhibition of necrosis by a candidate compound of the present invention correlates with a steady state level of protein synthesis. In another embodiment, inhibition of expression of pro-necrotic cytokines or hormones in a target cell by a candidate compound of the present invention correlates with a steady state level of protein synthesis.

In another embodiment, the present invention provides a method of testing a candidate compound for an ability to inhibit protein synthesis dependent inflammation, comprising the steps of contacting a cell with a candidate compound; and measuring the level of a SMN complex component in the cytoplasm of a cell, the nucleus of a cell, or a combination thereof, whereby, if a candidate compound increases the amount of the SMN complex component in the nucleus, decreases the amount of the SMN complex component in the cytoplasm, or a combination thereof, then the compound exhibits an ability to inhibit protein synthesis. In another embodiment, the present invention further provides detection of pro-inflammatory cell derived compounds (e.g. IL-1, IL-6, TNF-$\alpha$, and TGF-$\beta$) that are measured according to methods known to one of skill in the art.

In another embodiment, inhibition of protein synthesis is measured according to the methods of the present invention in cells secreting pro-inflammatory compounds. In another embodiment, induction of protein synthesis is measured according to the methods of the present invention in cells secreting pro-inflammatory compounds. In another embodiment, ability to decrease protein synthesis correlates with ability to induce the expression of pro-inflammatory cytokines in a target cell. In another embodiment, ability to inhibit protein synthesis correlates with ability to induce the expression of pro-inflammatory cytokines in a target cell. In another embodiment, ability to induce protein synthesis correlates with ability to induce the expression of pro-inflammatory cytokines in a target cell. In another embodiment, ability to increase protein synthesis correlates with ability to induce the expression of pro-inflammatory cytokines in a target cell.

In another embodiment, induction of inflammation by a candidate compound of the present invention correlates with a steady state level of protein synthesis. In another embodiment, induction of expression of pro-inflammatory cytokines in a target cell by a candidate compound of the present invention correlates with a steady state level of protein synthesis. In another embodiment, inhibition of inflammation by a candidate compound of the present invention correlates with a steady state level of protein synthesis. In another embodiment, inhibition of expression of pro-inflammatory cytokines in a target cell by a candidate compound of the present invention correlates with a steady state level of protein synthesis.

In another embodiment, the method of the present invention provides a method for screening for an inhibitor of protein synthesis, comprising the steps of contacting a cell with a candidate compound and measuring a level of an SMN complex component in the cytoplasm. In another embodiment, the method of the present invention provides a method for testing an inhibitor of protein synthesis, comprising the steps of contacting a cell with a candidate compound and measuring a level of an SMN complex component in the cytoplasm. In another embodiment, the method of the present invention further provides setting a threshold level of an SMN complex component in the cytoplasm in steady state (control treatment (FIG. 2)). In another embodiment, the method of the present invention provides that contacting a cell with a protein synthesis inhibitor causes a decline in the levels of an SMN complex component in the cytoplasm of the treated cells compared to the control cells.

In another embodiment, the method of the present invention provides a method for screening for an inhibitor of protein synthesis, comprising the steps of contacting a cell with a candidate compound and measuring an SMN complex component in the nucleus. In another embodiment, the method of the present invention provides a method for testing an inhibitor of protein synthesis, comprising the steps of contacting a cell with a candidate compound and measuring an SMN complex component in the nucleus.

In another embodiment, the present invention provides a method for screening for an inhibitor of protein synthesis, comprising the steps of contacting a cell with a candidate compound and measuring an SMN complex component in the nucleus. In another embodiment, the present invention provides a method for testing an inhibitor of protein synthesis, comprising the steps of contacting a cell with a candidate compound and measuring an SMN complex component in the nucleus. In another embodiment, the method of the present invention further provides setting a threshold level of an SMN complex component in the nucleus in steady state (control treatment (FIG. 2)). In another embodiment, the method of the present invention provides that contacting a cell with a protein synthesis inhibitor causes an incline in the levels of an SMN complex component in the nucleus of the treated cells compared to the control cells.

In one embodiment, the invention provides a method of identifying SMN complex components, which comprises visualizing the probed SMN complex components. In another embodiment, visualization of an SMN complex component is carried out by exposing the labeled specimen to a film. In another embodiment, visualization of an SMN complex component is performed using a fluorescent microscope. In another embodiment, visualization of an SMN complex component is performed using a confocal microscope. In another embodiment, visualization of an SMN complex component is performed using a transmission electron microscope (TEM). In another embodiment, visualization of an SMN complex component is performed using a scanning electron microscope (SEM). In another embodiment, visualization of an SMN complex component is performed using a reflection electron microscope (REM). In another embodiment, visualization of an SMN complex component is performed using a scanning transmission electron microscope (STEM). In another embodiment, a light microscope is used for visualization of SMN complex components, while in another embodiment; the signal is detectable using the naked eye. In another embodiment, the results of the above mentioned visualization methods can be further recorded and/or visualized on a charge-coupled device (CCD) camera. In another embodiment, a back-illuminated, cooled, CCD camera is used for luminescent detection. In another embodiment, color CCD cameras as well as dual-photon lasers are used for ultra-high-resolution imaging of a fluorescent protein.

In another embodiment, the invention provides means of quantifying the probed SMN complex components.

In another embodiment, quantification is assessed by a fluorometer. In another embodiment digital images are collected. In another embodiment digital images are collected from at least two fields in each well. In another embodiment digital images are collected from at least three fields in each well. In another embodiment digital images are collected from at least four fields in each well. In another embodiment digital images are collected from at least four fields in each well. In another embodiment digital images are collected from at least five fields in each well. In another embodiment digital images are collected from six fields in each well (example 2).

In another embodiment, the methods of the present invention provide means of analyzing the digital images of the invention.

In another embodiment, means of analyzing the digital images comprise computer software based on algorithms for multiple parameters. In another embodiment, the methods of the present invention provide that multiple parameters comprise at least two parameters. In another embodiment, the multiple parameters comprise nuclear and cytoplasmic florescence intensities (example 2). In another embodiment, the multiple parameters comprise relative nuclear and cytoplasmic florescent intensities (example 2). In another embodiment, the multiple parameters comprise nuclear and cytoplasmic chemiluminescent or gold label intensities. In another embodiment, the multiple parameters comprise nuclear and cytoplasmic radioactive label intensities. In another embodiment, multiple parameters further comprise number, size and signal intensity of a SMA complex component. In another embodiment, multiple parameters further comprise number, size and signal intensity of Gems.

In another embodiment, chemiluminescent detection comprises an enzyme which provides enzymatic amplification. In another embodiment, the enzyme which provides enzymatic amplification is horseradish peroxidase. In another embodiment, the enzyme which provides enzymatic amplification is alkaline phosphatase. In another embodiment, the enzyme which provides enzymatic amplification is β-galactosidase.

Figure 2:
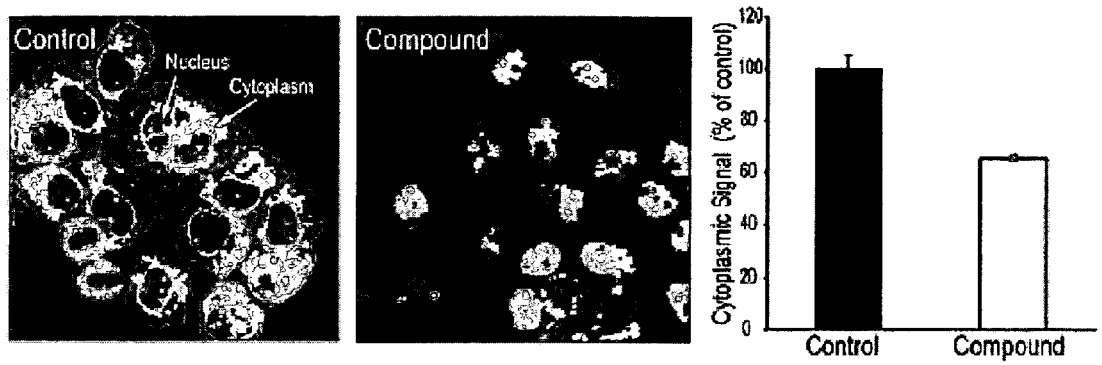
FIG. 2A and FIG. 2B shows an immunostaining micrograph [×20] identifying alterations in SMN sub-cellular localization.
FIG. 2C shows a bar graph which represents quantitation of the average changes in cytoplasmic fluorescence intensity in control (DMSO treated cells) (black bars) and in cells treated for 4 hours with a compound having a significant change in SMN sub-cellular distribution (white bars).

In another embodiment, the method of the present invention provides nucleus boundaries identification. In another embodiment, the method of the present invention provides that nucleus boundaries are identified according to nuclear membrane staining. In another embodiment, the method of the present invention provides a separate channel to define the boundary of each nucleus. In another embodiment, the method of the present invention provides that DAPI-stained images are collected in a separate channel to define the boundary of each nucleus (example 1). In another embodiment a change in SMN sub-cellular localization is examined directly (FIG. 2).

In another embodiment, the present invention provides a method of quantitatively measuring the amount of a SMN complex component in the nucleus and in the cytoplasm.

In another embodiment, the present invention provides a method for comparative assessment of the amounts of a SMN complex component in the nucleus and in the cytoplasm. In another embodiment, the present invention provides a method for comparative assessment of the relative amounts of a SMN complex component in the nucleus and in the cytoplasm.

In another embodiment, the present invention provides a method for screening a library of compounds for ability to treat a disease associated with protein synthesis inhibition, comprising the steps of contacting a plurality of cells or cell samples with potential inhibitors of protein synthesis, and measuring the level of SMN complex in the cytoplasm of the cell, the nucleus of the cell, or a combination thereof, whereby, if a compound in the library increases the amount of the SMN complex in the nucleus, decreases the amount of the SMN complex in the cytoplasm, or a combination thereof, then the compound exhibits an ability to inhibit protein synthesis. In another embodiment, the present invention provides a method for testing a library of compounds for ability to treat a disease associated with protein synthesis inhibition, comprising the steps of contacting a plurality of cells or cell samples with potential inhibitors of protein synthesis, and measuring the level of SMN complex in the cytoplasm of the cell, the nucleus of the cell, or a combination thereof, whereby, if a compound in the library increases the amount of the SMN complex in the nucleus, decreases the amount of the SMN complex in the cytoplasm, or a combination thereof, then the compound exhibits an ability to inhibit protein synthesis.

In another embodiment, the disease associated with protein synthesis inhibition is Alzheimer's disease. In another embodiment, protein synthesis is significantly altered in Alzheimer's disease. In another embodiment this impairments contributes to Alzheimer's disease pathogenesis. In another embodiment, the disease associated with protein synthesis inhibition is mild cognitive impairment. In another embodiment, protein synthesis inhibition is a factor in regulating whether cells maintain homeostasis in response to oxidative damage, or conversely whether oxidative stress is induced by oxidative damage.

In another embodiment, the disease associated with protein synthesis inhibition is a viral disease. In another embodiment, the virus inhibits protein synthesis in the host cell. In another embodiment, the disease associated with protein synthesis inhibition is Newcastle disease. In another embodiment, Newcastle disease is induced by Newcastle disease virus-(NDV). In another embodiment, NDV induces inhibition of host cell protein and RNA synthesis.

In another embodiment, a picornavirus virus inhibits protein synthesis in a host cell. In another embodiment, the disease associated with protein synthesis inhibition is polio. In another embodiment, polio disease is induced by poliovirus. In another embodiment, poliovirus induces inhibition of host cell protein synthesis.

In another embodiment, the disease associated with protein synthesis inhibition is cancer. In another embodiment, the cancer associated with protein synthesis inhibition is breast cancer. In another embodiment, metastatic breast carcinomas are associated with protein synthesis inhibition. In another embodiment, metastatic breast carcinomas in lymph nodes are associated with protein synthesis inhibition.

In another embodiment, the present invention provides a kit for measuring protein synthesis inhibitors in a cell. In another embodiment, the kit of present invention comprises an SMN complex component relocalization measuring reagents.

In another embodiment, the kit of present invention comprises a ligand selective for a SMN complex component.

In another embodiment, the kit of present invention comprises an SMN complex component relocalization measuring reagents. In another embodiment, the kit of present invention comprises a ligand selectively capturing a SMN complex component. In another embodiment, the ligand of the invention binds Gem. In another embodiment, the ligand of the invention specifically binds a Gemin protein.

In another embodiment, the kit of the present invention comprises an antibody.

In another embodiment the kit of the present invention comprises a polyclonal antibody. In another embodiment, the kit of the present invention comprises a monoclonal antibody. In another embodiment, the kit of the present invention comprises a monovalent Fab fragments. In another embodiment, the kit of the present invention comprises a Bivalent miniantibody.

In another embodiment, the kit of the present invention comprises a multiple engineered specificity antibody. In another embodiment, the kit of the present invention comprises a bispecific antibodies which contain two different binding specificities fused together. In another embodiment, bispecific antibodies of the invention bind to two adjacent epitopes on a single target antigen. In another embodiment, bispecific antibodies of the invention bind to two adjacent epitopes on the SMA complex. In another embodiment, bispecific antibodies of the invention cross-link two different antigens. In another embodiment, bispecific antibodies of the present invention are produced by fusion of two hybridoma cell lines into a single 'quadroma' cell line. In another embodiment, effective methods to couple two different Fab modules of the invention incorporate chemical conjugation. In another embodiment, effective methods to couple two different Fab modules of the invention incorporate genetic conjugation. In another embodiment, effective methods to couple two different Fab modules of the invention incorporate fusion to adhesive heterodimeric domains.

In another embodiment, the kit of the present invention comprises a bifunctional antibody. In another embodiment, the antibody of the present invention is fused to radio labeled moiety. In another embodiment, the antibody of the present invention is fused to an enzyme.

In another embodiment, the kit of the present invention comprises an antibody derived from antibody libraries. In another embodiment, the kit of the present invention comprises an antibody which is a specific high-affinity antibody selected by linking phenotype (binding affinity) to genotype, thereby allowing simultaneous recovery of the gene encoding the selected antibody.

In another embodiment, the kit of the present invention comprises an antibody composed of a single-chain Fv fragments. In another embodiment, the single-chain Fv fragments antibody of the present invention contain a complete binding site and consist of the individual heavy and light chain V domain. In another embodiment, the single-chain Fv fragments antibody of the present invention is linked to a single protein by a hydrophilic and flexible polypeptide linker. In another embodiment, the single-chain Fv fragments antibody of the present invention additionally include also a His tag. In another embodiment, the single-chain Fv fragments antibody of the present invention additionally includes an immunodetection epitope. In another embodiment, the single-chain Fv fragments antibody of the present invention additionally includes a protease specific cleavage site. In another embodiment, the linker of the variable region domains (carboxyl ter-minus of the VL sequence to the amino terminus of the VH sequence) has to be long enough to span the distance from the C-terminus of one domain to the N-terminus of the second domain (about 3.5 nm).

In another embodiment, the kit of the present invention comprises an antibody which binds a protein within the SMN complex. In another embodiment, the kit of the present invention comprises a monoclonal anti-SMN component antibody. In another embodiment, the kit of the present invention comprises an anti-SMN monoclonal 2B1 antibody. In another embodiment, the kit of the present invention comprises 2B1 antibody which binds Gems. In another embodiment, the kit of the present invention comprises 2B1 antibody which binds cytoplasmic Gems. In another, embodiment, the kit of the present invention comprises 2B1 antibody which binds nuclear Gems. In another embodiment, the kit of the present invention comprises an anti-Gemin1 antibody. In another embodiment, the kit of the present invention comprises an anti-Gemin1 antibody. In another embodiment, the present invention comprises an anti-Gemin2 antibody. In another embodiment, the kit of the present invention comprises an anti-Gemin3 antibody. In another embodiment, the kit of the present invention comprises an anti-Gemin4 antibody. In another embodiment, the kit of the present invention comprises an anti-Gemin5 antibody. In another embodiment, the kit of the present invention comprises an anti-Gemin6 antibody. In another embodiment, the kit of the present invention comprises an anti-Gemin7 antibody.

In another embodiment, the kit of the present invention comprises a labeled ligand. In another embodiment, the kit of the present invention comprises a labeled antibody. In another embodiment, the labeled antibody is a fluorescent labeled antibody as described hereinabove.

In another embodiment, the kit of the present invention comprises a plasmid encoding a SMN complex component fused to a fluorescent probe. In another embodiment, the fluorescent probe is selected from the fluorescent proteins described hereinabove. In another embodiment, plasmid comprises a Gemin protein fused to a fluorescent probe of the invention.

In another embodiment, the kit of the present invention comprises a radioactive label. In another embodiment, the kit of the present invention comprises a ligand radioactively labeled with $^{32}P$. In another embodiment, the kit of the present invention comprises an antibody radioactively labeled with $^{32}P$. In another embodiment, the kit of the present invention comprises a ligand radioactively labeled with $^{125}I$. In another embodiment, the kit of the present invention comprises an antibody radioactively labeled with $^{125}I$. In another embodiment, the kit of the present invention comprises a ligand attached to chemiluminescent label. In another embodiment, the kit of the present invention comprises an antibody attached to a chemiluminescent label. In another embodiment, the kit of the present invention comprises a ligand conjugated to a chemiluminescent label. In another embodiment, the kit of the present invention comprises an antibody conjugated to a chemiluminescent label. In another embodiment, the kit of the present invention comprises a ligand conjugated to a gold label. In another embodiment, the kit of the present invention comprises an antibody conjugated to a gold label.

In another embodiment, the kit of the present invention comprises buffers. In another embodiment, buffers of the present invention comprise the reagents of the present invention. In another embodiment, the kit of the present invention comprises cell fixation reagents. In another embodiment, the fixation reagent of the present invention is an alcohol. In another embodiment, the fixation reagent of the present invention is methanol. In another embodiment, the fixation reagent of the present invention is ethanol. In another embodiment, the fixation reagent of the present invention is paraformaldehyde. In another embodiment, the fixation reagent of the present invention is glutaraldehyde. In another embodiment, the fixation reagent of the present invention is an aldehyde. In another embodiment, the fixation reagent of the present invention is dimethylsuberimidate.

In another embodiment, the kit of the present invention comprises a permeability enhancing agents such as detergents. In another embodiment, the permeability enhancing agent of the present invention is saponin. In another embodiment, the permeability enhancing agent of the present invention is tween.

In another embodiment, the kit of the present invention comprises an enzyme conjugated to avidin. a ligand labeled with a hapten. In another embodiment, the kit of the present invention comprises a biotinylated ligand. In another embodiment, the kit of the present invention comprises a label conjugated to avidin. In another embodiment, the kit of the present invention comprises an enzyme conjugated to avidin.

In another embodiment, the kit of the present invention comprises an enzyme which creates a detectable event (e.g., chemiluminescent, colorimetric or fluorescent).

In another embodiment, the kit of the present invention comprises alkaline phosphatase. In another embodiment, the kit of the present invention comprises β-galactosidase. In another embodiment, the kit of the present invention comprises peroxidase. In another embodiment, the kit of the present invention comprises horseradish peroxidase.

In another embodiment, the kit of the present invention comprises a secondary labeled antibody specifically identifying the primary antibody.

In another embodiment, the kit of the present invention further comprises a nuclear dye. In another embodiment, the kit of the present invention further comprises Azur A. In another embodiment, the kit of the present invention further comprises hematoxylin. In another embodiment, the kit of the present invention further comprises Methyl Violet. In another embodiment, the kit of the present invention further comprises Phloxine B. In another embodiment, the kit of the present invention further comprises Pyronin Y. In another embodiment, the kit of the present invention further comprises Safranin O. In another embodiment, the kit of the present invention further comprises a cytoplasmic dye. In another embodiment, the kit of the present invention further comprises a cytoplasmic membrane dye. In another embodiment, the kit of the present invention further comprises a nuclear membrane dye. In another embodiment, the kit of the present invention further comprises DAPI (example 1). In another embodiment, the kit of the present invention further comprises a sub-cellular dye as will be readily known to one of skill in the art.

In another embodiment, the kit of the present invention further comprises a multi-well plate. In another embodiment, a multi-well plate of the present invention comprises 96 wells. In another embodiment, a multi-well plate of the present invention comprises 384 wells. In another embodiment, a multi-well plate of the present invention comprises 1536 wells. In another embodiment, a multi-well plate of the present invention comprises from 2-5000 wells. In another embodiment, a multi-well plate of the present invention comprises from 20-3000 wells. In another embodiment, a multi-well plate of the present invention comprises from 96-2000 wells.

In another embodiment, the system of the present invention measures protein synthesis inhibitors.

In another embodiment, the system of the present invention screens protein synthesis inhibitors. In another embodiment, the system of the present invention comprises the kit of the present invention as described hereinabove. In another embodiment, the system of the present invention comprises visualization means. In another embodiment, the system of the present invention tests protein synthesis inhibitors. In another embodiment, the system of the present invention comprises the kit of the present invention as described hereinabove. In another embodiment, the system of the present invention comprises visualization means.

In one embodiment, the system of the present invention comprises an apparatus for exposing the screen of the present invention to a film. In another embodiment, the system of the present invention comprises a fluorescent microscope. In another embodiment, the system of the present invention comprises a confocal microscope. In another embodiment, the system of the present invention comprises a transmission electron microscope. In another embodiment, the system of the present invention comprises a scanning electron microscope. In another embodiment, the system of the present invention comprises a reflection electron microscope. In another embodiment, the system of the present invention comprises a scanning transmission electron microscope. In another embodiment, the system of the present invention comprises a light microscope. In another embodiment, the system of the present invention comprises a charge-coupled device (CCD) camera. In another embodiment, the system of the present invention comprises a back-illuminated, cooled, CCD camera. In another embodiment, the system of the present invention comprises a color CCD camera. In another embodiment, the system of the present invention comprises a dual-photon laser.

In another embodiment, the system of the present invention comprises a fluorometer. In another embodiment, the system of the present invention comprises a computer which digitally records the microscopically captured images. In another embodiment, the system of the present invention comprises a computer which digitally records the CCD camera captured images.

In another embodiment, the system of the present invention comprises computer software.

In another embodiment, the computer software analyzes the digital images collected from at least two fields in each well. In another embodiment, the computer software analyzes the digital images collected from at least three fields in each well. In another embodiment, the computer software analyzes the digital images collected from at least four fields in each well. In another embodiment, the computer software analyzes the digital images collected from at least five fields in each well. In another embodiment, the computer software analyzes the digital images collected from at least six fields in each well. In another embodiment, the computer software analyzes the digital images collected from six fields in each well.

In another embodiment, the system of the present invention comprises computer software based on algorithms for multiple parameters. In another embodiment, the multiple parameters comprise at least two parameters. In another embodiment, the multiple parameters comprise nuclear and cytoplasmic florescent intensities. In another embodiment, the multiple parameters comprise relative nuclear and cytoplasmic florescent intensities. In another embodiment, the multiple parameters comprise nuclear and cytoplasmic chemiluminescent or gold label intensities. In another embodiment, the multiple parameters comprise nuclear and cytoplasmic radioactive label intensities. In another embodiment, the multiple parameters further comprise number, size and signal intensity of SMA complex components. In another embodiment, multiple parameters further comprise number, size and signal intensity of Gems.

EXPERIMENTAL DETAILS SECTION

Materials and Experimental Methods

Compounds

A library of about 5,000 pure bioactive chemicals that includes FDA-approved drugs, known inhibitors and activators of diverse enzymes and receptors, and pure natural compounds was assembled from commercial sources (Microsource Diversity, Tocris, Sigma/Aldrich and other suppliers). Cycloheximide, trichostatin A, valproic acid and scriptaid were purchased from Sigma Chemical Co. HDAC inhibitor I and apicidin were from EMD biosciences.

Cell Culture and Treatments

HeLa PV were cultured in Dulbecco's modified Eagle's medium (Invitrogen) supplemented with 10% fetal bovine serum (Invitrogen). For screening, cells were seeded onto 384-well plates or, for specific experiments, on glass coverslips the day before treatment. Compounds were added directly into the culture medium to the indicated concentration and the cells were then maintained at 37° C. in a 5% CO2 humidified atmosphere for the duration of the treatment. Dispensing of compounds and other automatic liquid handling steps were performed with a Beckman FX multi-channel system equipped with Hudson Crane robotic systems.

Antibodies

The following mouse monoclonal antibodies were used for indirect immunofluorescence: 2B1 (anti-SMN), 2E17 (anti-Gemin2), 12H12 (anti-Gemin3), 10G11 (anti-Gemin5), 6E2 (anti-Gemin7), 10E10 (anti-PABP), 6BG10 (anti-FXR1), Y12 (anti-Sm) and 9H10 (anti-hnRNP A1). An affinity-purified rabbit polyclonal antibody was used to detect Gemin6.

Indirect Immunofluorescence Microscopy

Indirect immunofluorescence on HeLa PV cells was performed as follows: HeLa cells, plated on glass coverslips, were briefly washed with PBS, fixed in 2% formaldehyde/PBS for 20 minutes at room temperature, permeabilized in 0.5% Triton X-100/PBS for 5 min at room temperature. Cells were blocked in 3% bovine serum albumin for 1 hour at room temperature. Double-label immunofluorescence experiments were performed by separate sequential incubations of each primary antibody, diluted in PBS containing 3% bovine serum albumin, followed by the specific secondary coupled to fluorescein isothiocyanate or TXRD. All incubations were at room temperature for 1 hour. Indirect epifluorescence microscopy was performed with a Nikon Eclipse E800 microscope. Digital images were collected with a Cook Sensicam high performance camera and processed with the IP laboratory software. Processing of samples for immunofluorescence microscopy on cells cultured in 384-well plates was automated and performed with the aid of microplate washers (ELX405, Bio-Tek) in a similar manner to that previously used for individual samples on glass slides. The cells were also stained with DAPI to allow definition of the nucleus in each cell. Digital images were acquired with an automated microscopy and analysis system (IN Cell Analyzer 1000, GE Healthcare). Images were analyzed using automated algorithms with parameters set to calculate mean pixel intensity in each nucleus (defined by DAPI staining and acquired in a separate channel), cytoplasm, and total cell, as well as the relevant calculated ratios of these values.

RNA Interference

Transient RNAi was performed as follows: 21-nt RNA duplexes (siRNAs) were designed to target SMN or Gemin2-6 mRNAs. For each target transcript, at least five siRNAs were designed and tested and, in general, found to behave similarly in all subsequent analyses. The following siRNA sequences yielded the most efficient protein knockdowns of each target: GAAGAAUACUGCAGCUUCC (SEQ ID NO: 8) for SMN; GCAGCUCAAUGUCCAGAUG (SEQ ID NO: 9) for Gemin2; GGCUUAGAGUGUCAUGUCU (SEQ ID NO: 10) for Gemin3; ACUCCCCAGUGAGAC-CAUU (SEQ ID NO: 11) for Gemin4; GCAUAGUG-GUGAUAAUUGA (SEQ ID NO: 12) for Gemin5 and AAC-UACAGACCCAGUCUCGC (SEQ ID NO: 13) for Gemin6. In addition, an siRNA initially designed to target Y14, a component of the exon junction complex, which failed to produce any protein reduction within 44 h, was used as a control (CCCGGACCACAACGCUCUG (SEQ ID NO: 14)). All siRNAs were chemically synthesized and purified by Dharmacon Research. Transfections of siRNAs into HeLa PV cells were performed using Oligofectamine™ (Invitrogen) as specified by the manufacturer. Transfected cells were analyzed 40-44 h post-transfection.

Example 1

SMN Complex Composition

In order to determine whether Gems are affected by changes in the composition of the complex, the amount of several Gemins was reduced, one at a time, by RNA interference. The morphology of Gems was monitored by immunofluorescence microscopy using the anti-SMN monoclonal antibody 2B1.

Reduction of Gemin3 or Gemin4 caused large changes in the size, number and SMN signal intensity of Gems (FIG. 1a). The effect of the treatments was quantified with software analysis of the collected images from a large number of cells. The results indicated a two-fold increase in both signal intensity as well as gem number in each case (FIG. 1b). Thus, changes in the SMN complex are reflected by changes in the morphology of Gems.

Example 2

Screening Assay

Based on the results obtained in Example 1, a library of ~5,000 biologically active small molecules was screened on HeLa cells in 384-well plates. Each well was incubated with a different compound (at 10 µM) and the cells were processed for indirect immunofluorescence. Digital images were collected from six fields in each well and analyzed using imaging algorithms for multiple parameters including relative nuclear and cytoplasmic intensities, and number, size and signal intensity of Gems. DAPI-stained images were collected in a separate channel to define the boundary of each nucleus. Images of individual fields in wells were flagged by the software as showing a significant change in SMN sub-cellular localization. These individual wells were examined directly, and active compounds were re-tested for verification (FIG. 2).

Example 3

Redistribution of SMN from the Cytoplasm to the Nucleus

Figure 3:
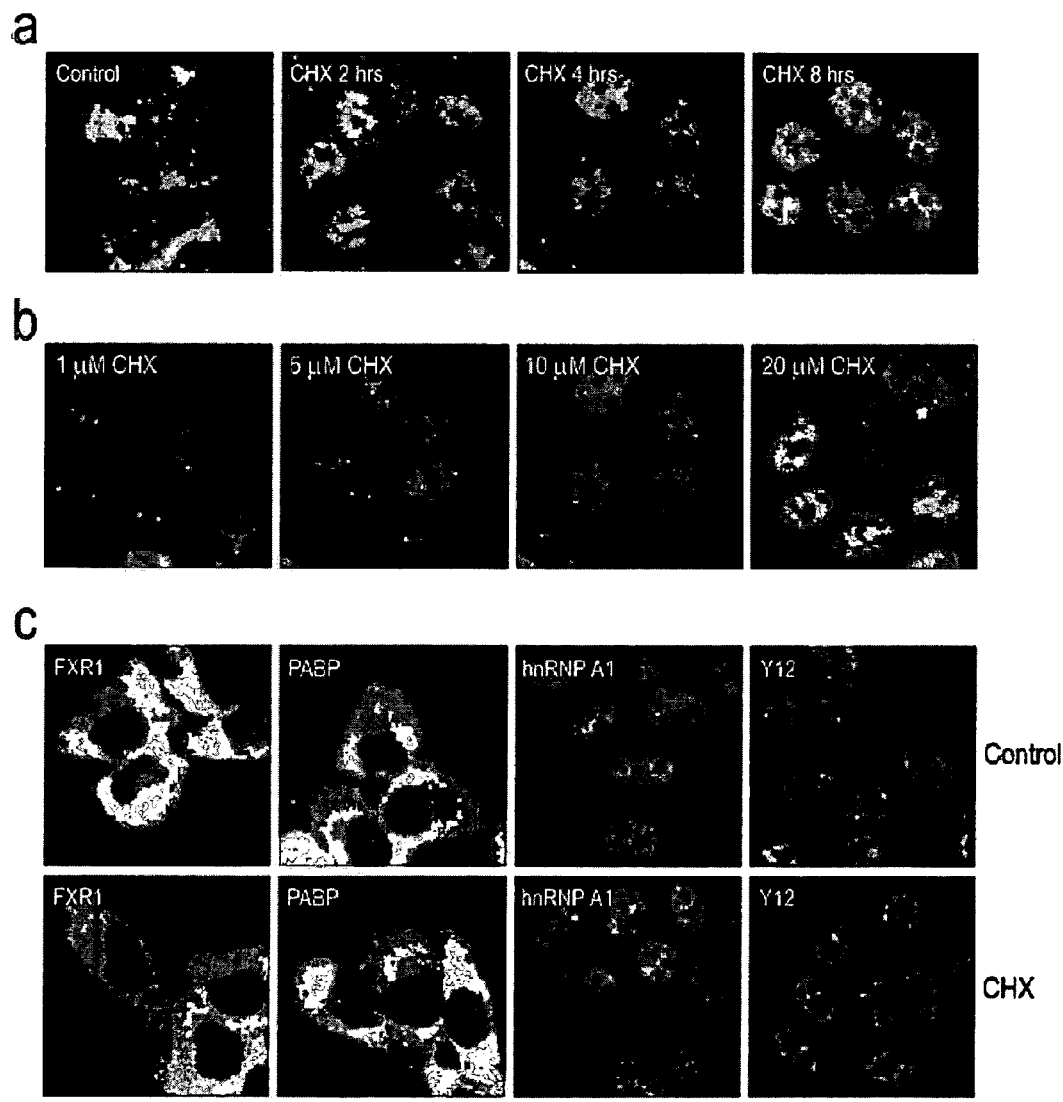
FIG. 3A shows an immunostaining micrograph of SMN in control HeLa PV cells and following treatment with 10 μM cycloheximide (CHX) for the indicated times. Control cells were treated with DMSO at the same final concentration as that used to dissolve CHX.
FIG. 3B shows a microscopic immunostaining micrograph of SMN localization in HeLa cells treated with 5-20 µM cycloheximide and immunostained after 4 hours of treatment.
FIG. 3C shows a microscopic immunostaining micrograph of FXR1, PABP, hnRNP A1 and Sm proteins (snRNPs) in control HeLa cells (upper panel) and after 6 hrs of 10 µM CHX treatment (lower panel).
Figure 6:
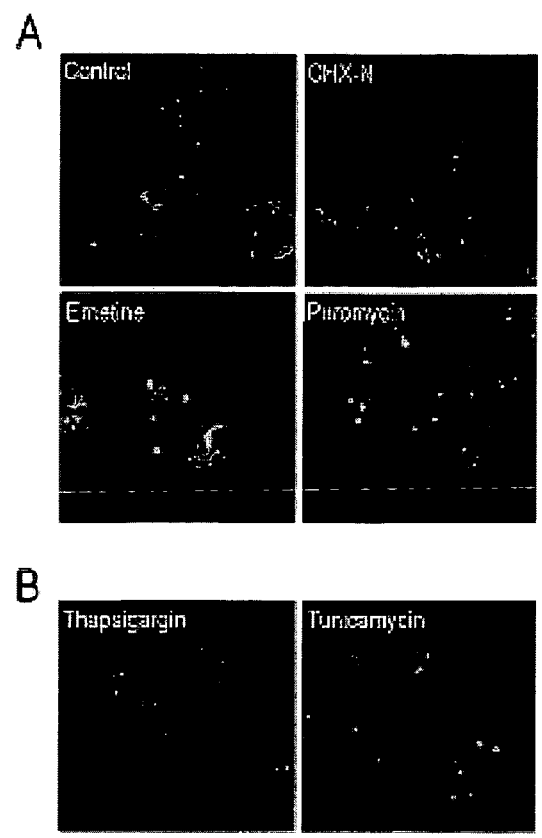
FIG. 6 shows an immunostaining micrograph of SMN localization.

The previous Examples screened compounds that caused changes in Gems. However, it was noticed that several compounds produced a massive redistribution of SMN from the cytoplasm to the nucleus within a relatively short time (2-6 hours) of treatment (according to the materials and methods of example 2). The most striking accumulation of SMN in the nucleus was observed after treatment with the commonly used protein synthesis inhibitor, cycloheximide (CHX). The effect of CHX was evident after only 2 hours of treatment and there was little SMN detected in the cytoplasm after 8 or more hours of treatment. CHX effect on redistribution of SMN from the cytoplasm to the nucleus was concentration-dependent exhibiting a clear effect even at low micromolar concentrations (0.1-40 µM) (FIG. 3a, b). The nuclear accumulation of SMN did not require complete inhibition of protein synthesis and was proportional to the extent of inhibition of protein synthesis. An inactive cycloheximide analog, cycloheximide-N-ethylethanoate, did not show any effect (FIG. 6).

The accumulation of SMN in the nucleus and its disappearance from the cytoplasm under conditions of protein synthesis inhibition indicates that it represents SMN protein that translocated from the cytoplasm. Other protein synthesis inhibitors, including emetine, an irreversible inhibitor of translation elongation, and the peptide chain terminator, puromycin, showed the same effect as cycloheximide, demonstrating that it is a general consequence of protein synthesis inhibitors (FIG. 6).

The effect of several compounds that do not directly inhibit translation, but rather cause translation inhibition as an indirect effect was monitored. Inducers of endoplasmic reticulum stress, such as thapsigargin and tunicamycin elicit the unfolded protein response, which leads to a reduction in general protein translation through the phosphorylation of eIF2α17. Treatment of cells with thapsigargin or tunicamycin caused SMN to accumulate in the nucleus (FIG. 6B) (, although the effect was not as complete as that seen after treatment with high levels of CHX, consistent with the fact that protein synthesis is not shut down and selective translation of a class of mRNAs continues under these conditions.

Example 4

The Protein Synthesis Inhibitor-Induced Nuclear Accumulation of SMN is Specific The protein synthesis inhibitor-induced nuclear accumulation of SMN is not the result of general cell toxicity as no reduction in cell viability was monitored even after an overnight treatment of these cells with 10 µM CHX, conditions in which all of the SMN was localized to the nucleus. In addition, the nuclear accumulation is specific to the localization of SMN and not the result of general mis-localization of proteins, as the localization of many other, both nuclear and cytoplasmic proteins that were examined, including the RNA-binding proteins hnRNP A1, poly(A)-binding protein (PABP), FXR1 and snRNPs, was not significantly affected (FIG. 3c).

Figure 7:
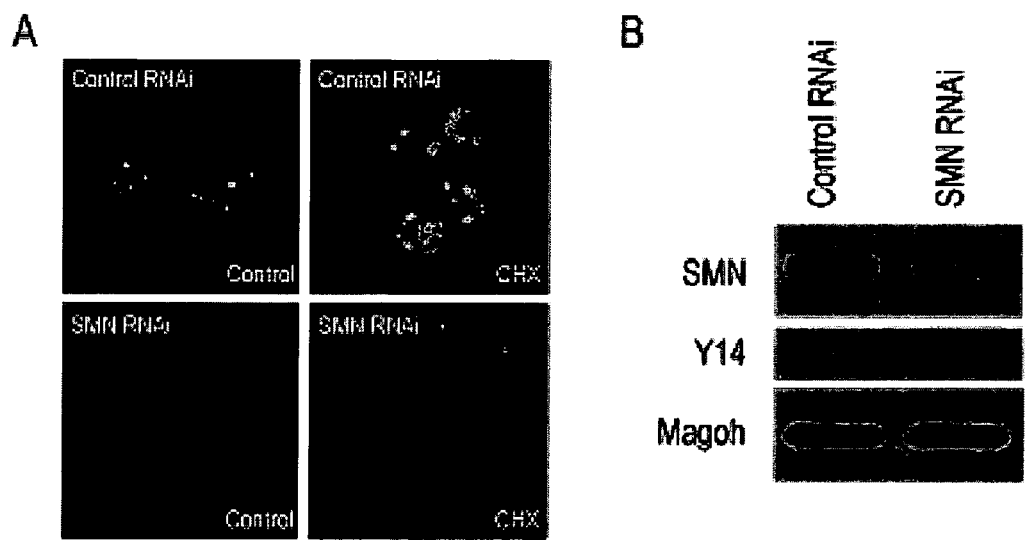
FIG. 7 shows an immunostaining micrograph of SMN localization in HeLa PV cells stably transfected with a non-targeting shRNA (upper panels) and in cells stably transfected with an shRNA targeting SMN (lower panels). Both cell lines were treated with DMSO as control at the same final concentration as that used to dissolve CHX and following treatment with 10 µM cycloheximide (CHX) for 6 hours as indicated.

Furthermore, the effect was reversible as SMN staining gradually re-appeared in the cytoplasm when cells were washed and placed in fresh medium devoid of cycloheximide. A similar effect of protein synthesis inhibitors was also observed in several other cell types and in other species, including U2OS cells and both human and mouse fibroblasts, and was independent of the amount of SMN they contained. Hela cells with reduced SMN by RNAi, compared to control cells expressing a non-targeting shRNA, showed a similar effect (FIG. 7).

Example 5

Gemins Also Relocate to the Nucleus

Figure 4:
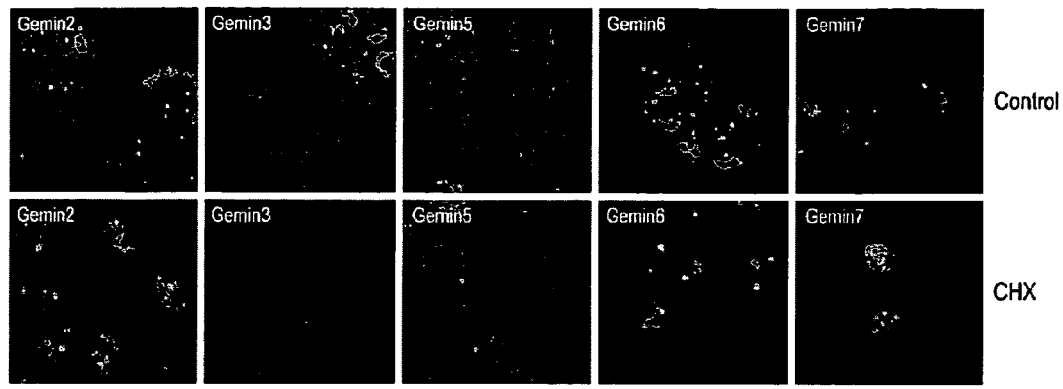
FIG. 4 shows an immunostaining micrograph of sub-cellular localization of an SMN complex component in control HeLa cells and in CHX treated cells. Immunostaining of Gemins 2, 3, 5, 6 and 7 in control DMSO treated cells is shown in the upper panel. Immunostaining of Gemins 2, 3, 5, 6 and 7 in cells treated for 6 hours with 10 µM CHX is shown in the lower panel.

According to the materials and methods of Example 2, treated cells were stained with antibodies to each of the Gemins. The results indicate that in addition to SMN, several of the Gemins, with the exception of Gemin3 and Gemin5, also relocated to the nucleus (FIG. 4).

Thus, CHX treatment causes most of the components of the SMN complex to accumulate in the nucleus, and not just SMN alone. This further indicates that the response is a specific effect upon SMN and some associated proteins. Furthermore, the total amount of SMN in HeLa cells treated with CHX was similar to that found in untreated cells, showing that the SMN complexes that accumulated in the nucleus must have been translocated from the cytoplasm.

These observations were made after relatively short treatment times (4-6 hours). However, at longer times (>24 hr), nuclear translocation of SMN was observed for several other compounds. Notably, histone deacetylase (HDAC) inhibitors, including valproic acid (VPA), trichostatin A, scriptaid, apicidin and HDAC inhibitor 1, that caused the same effect as protein synthesis inhibitors (FIG. 5a).

These compounds showed strong toxicity and resulted in a large reduction in cell numbers. However, they do not cause inhibition of protein synthesis, indicating that their effect on the translocation of SMN works by a different, although possibly convergent, mechanism from that of the protein synthesis inhibitors.

Figure 5:
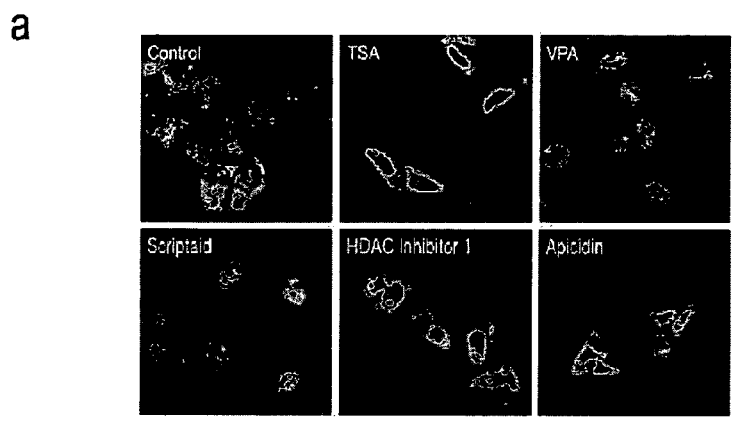
FIG. 5 shows an immunostaining micrograph of sub-cellular localization of an SMN complex component in control HeLa cells and in HDAC inhibitors treated cells.
Figure 5:
Figure 5:
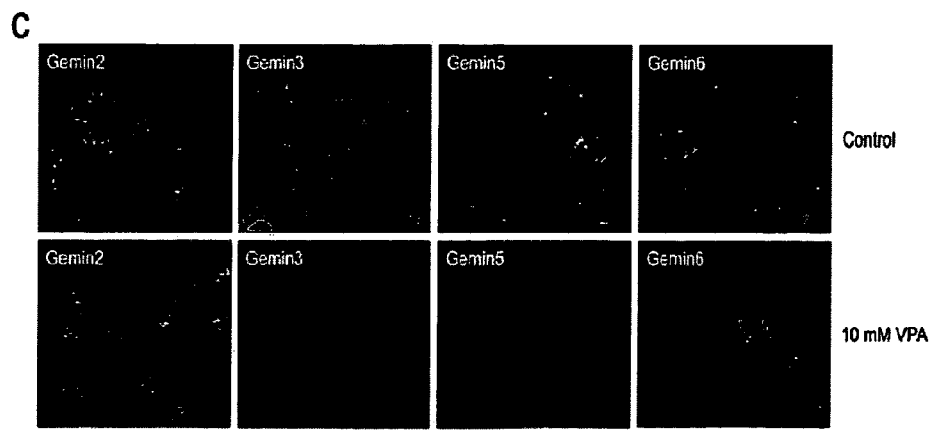

VPA also displayed a clear concentration dependence effect on the nuclear localization of SMN in addition to its specificity in relocalizing a subset of the SMN complex to the nucleus (FIGS. 5b and c). Namely, Gemin3 and Gemin5 remain predominantly cytoplasmic upon a 24 hour treatment with VPA. This further shows that SMN likely responds to these compounds in a similar manner.

Thus these experiments demonstrate that the cellular localization of the SMN complex is a dynamic and highly regulated process. Specifically, reduction in protein synthesis as a result of either direct interaction of inhibitors with the translation machinery or indirectly, as a consequence of ER stress, profoundly affects the SMN complex, translocating SMN and several of the complex components to the nucleus.

Although both translation inhibitors and HDAC inhibitors show a similar effect, the former class of compounds elicited the most rapid responses. The noticeable increase in the amount of the an SMN complex component in the nucleus, even at low doses of inhibitor that produce only a very small reduction in overall translation, indicates that even mild stresses that attenuate translation have an effect on the balance of the SMN complex.

It appears that the SMN complex either dissociates into Gemin3/5 and SMN, Gemin2, 6, 7 subunits upon inhibition of translation or these subunits are already mostly in the dissociated form and their localization in the cell is regulated differently.

What is claimed is:

1. A method for testing a candidate compound for an ability to inhibit protein synthesis in a cell, comprising the steps of:
contacting said cell with said candidate compound; and
measuring the level of a SMN complex component in the cytoplasm of said cell, the nucleus of said cell, or a combination thereof, whereby, if said candidate compound increases the amount of the SMN complex component in said nucleus, decreases the amount of the SMN complex component in said cytoplasm, or a combination thereof, then said compound exhibits an ability to inhibit protein synthesis.

2. The method of claim 1, wherein said cell is a eukaryotic cell.

3. The method of claim 1, wherein said method further comprises the step of contacting said cell with a ligand selective for said SMN complex component.

4. The method of claim 3, wherein said ligand is an antibody.

5. The method of claim 4, wherein said antibody is a monoclonal antibody.

6. The method of claim 4, wherein said antibody is a labeled antibody.

7. The method of claim 6, wherein said labeled antibody is a fluorescent labeled antibody.

8. The method of claim 3, wherein said ligand is a labeled ligand.

9. The method of claim 8, wherein said labeled ligand is a fluorescent labeled ligand.

10. The method of claim 1, wherein said SMN complex component is fused to a fluorescent probe.

11. The method of claim 1, wherein said SMN complex component is a Gem.

12. The method of claim 1, wherein said SMN complex component is a Gemin.

13. The method of claim 12, wherein said Gemin is Gemin 2, Genin 6, Gemin 7, or any combination thereof.

14. The method of claim 1, wherein the step of measuring comprises the use of visualization means to identify said SMN complex components.

15. The method of claim 14, wherein said visualization means comprise a microscope.

16. The method of claim 14, wherein said step of visualization of said SMN complex component further comprises the use of digital images.

17. The method of claim 16, wherein said digital images are analyzed using imaging algorithms for parameters comprising nuclear signal intensity and cytoplasmic signal intensity.

18. A method for testing a candidate compound for an ability to inhibit protein synthesis in a cell, comprising the steps of:
contacting said cell with said candidate compound; and
measuring a level of an SMN complex component in the nucleus of said cell, whereby, if said candidate compound increases the amount of the SMN complex component in said nucleus then said compound exhibits an ability to inhibit protein synthesis.

* * * * *